US008095209B2

(12) United States Patent
Flaherty

(10) Patent No.: US 8,095,209 B2
(45) Date of Patent: Jan. 10, 2012

(54) BIOLOGICAL INTERFACE SYSTEM WITH GATED CONTROL SIGNAL

(75) Inventor: J. Christopher Flaherty, Topsfield, MA (US)

(73) Assignee: BrainGate Co., LLC, Ponte Vedra Beach, FL (US)

(*) Notice: Subject to any disclaimer, the term of this patent is extended or adjusted under 35 U.S.C. 154(b) by 1777 days.

(21) Appl. No.: 11/316,807

(22) Filed: Dec. 27, 2005

(65) Prior Publication Data

US 2006/0241356 A1    Oct. 26, 2006

Related U.S. Application Data

(60) Provisional application No. 60/642,199, filed on Jan. 6, 2005.

(51) Int. Cl.
*A61B 5/04* (2006.01)

(52) U.S. Cl. ........................................ 600/544; 600/545

(58) Field of Classification Search .......... 600/544–545; 623/57
See application file for complete search history.

(56) References Cited

U.S. PATENT DOCUMENTS

| | | | |
|---|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,524,774 A | 6/1985 | Hildebrandt et al. |
| 4,557,257 A | 12/1985 | Fernandez et al. |
| 4,566,464 A | 1/1986 | Piccone et al. |
| 4,633,889 A | 1/1987 | Talalla et al. |
| 4,690,142 A | 9/1987 | Ross et al. |

(Continued)

FOREIGN PATENT DOCUMENTS

EP    0 911 061 A    4/1999

(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner* — Patricia Mallari
*Assistant Examiner* — Michael D'Angelo
(74) *Attorney, Agent, or Firm* — SoCal IP Law Group LLP; Steven C. Sereboff; M. Kala Sarvaiya

(57) ABSTRACT

Various embodiments of a biological interface system and related methods are disclosed. The biological interface system may comprise a sensor comprising a plurality of electrodes for detecting multicellular signals emanating from one or more living cells of a patient, a processing unit configured to receive the multicellular signals from the sensor and process the multicellular signals to produce a processed signal, and a signal gate configured to receive the processed signal from the processing unit and an alternative signal generated by the system, the signal gate being configured to transmit a control signal to a controlled device based on either the processed signal or the alternative signal. A monitoring unit may receive system data and process the system data to produce a system status signal. The system status signal may be used to determine which of the processed signal and the alternative signal is to be used as the control signal.

211 Claims, 4 Drawing Sheets

U.S. PATENT DOCUMENTS

| | | |
|---|---|---|
| 4,837,049 A | 6/1989 | Byers et al. |
| 4,865,048 A | 9/1989 | Eckerson |
| 4,878,913 A | 11/1989 | Aebischer et al. |
| 4,883,666 A | 11/1989 | Sabel et al. |
| 4,969,468 A | 11/1990 | Byers et al. |
| 5,037,376 A | 8/1991 | Richmond et al. |
| 5,081,990 A | 1/1992 | Deletis |
| 5,092,329 A | 3/1992 | Graupe et al. |
| 5,119,832 A | 6/1992 | Xavier |
| 5,121,747 A | 6/1992 | Andrews |
| 5,156,844 A | 10/1992 | Aebischer et al. |
| 5,178,161 A | 1/1993 | Kovacs et al. |
| 5,215,088 A | 6/1993 | Normann et al. |
| 5,325,862 A | 7/1994 | Lewis et al. |
| 5,325,865 A | 7/1994 | Beckman et al. |
| 5,330,516 A | 7/1994 | Nathan |
| 5,361,760 A | 11/1994 | Normann et al. |
| 5,413,611 A | 5/1995 | Haslam et al. |
| 5,423,877 A | 6/1995 | Mackey |
| 5,445,608 A | 8/1995 | Chen et al. |
| 5,458,631 A | 10/1995 | Xavier |
| 5,474,547 A | 12/1995 | Aebischer et al. |
| 5,476,441 A | 12/1995 | Durfee et al. |
| 5,549,656 A | 8/1996 | Reiss |
| 5,617,871 A | 4/1997 | Burrows |
| 5,638,826 A | 6/1997 | Wolpaw et al. |
| 5,687,291 A | 11/1997 | Smyth |
| 5,692,517 A | 12/1997 | Junker |
| 5,697,951 A | 12/1997 | Harpstead et al. |
| 5,702,432 A | 12/1997 | Chen et al. |
| 5,713,923 A | 2/1998 | Ward et al. |
| 5,724,987 A | 3/1998 | Gevins et al. |
| 5,735,885 A | 4/1998 | Howard, III et al. |
| 5,758,651 A | 6/1998 | Nygard et al. |
| 5,797,898 A | 8/1998 | Santini, Jr. et al. |
| 5,814,089 A | 9/1998 | Stokes et al. |
| 5,843,093 A | 12/1998 | Howard, III |
| 5,843,142 A | 12/1998 | Sultan |
| 5,855,801 A | 1/1999 | Lin et al. |
| 5,857,978 A | 1/1999 | Hively et al. |
| 5,873,840 A | 2/1999 | Neff |
| 5,928,228 A | 7/1999 | Kordis et al. |
| 5,938,688 A | 8/1999 | Schiff |
| 5,938,689 A | 8/1999 | Fischell et al. |
| 5,938,690 A | 8/1999 | Law et al. |
| 5,995,868 A | 11/1999 | Dorfmeister et al. |
| 6,001,065 A | 12/1999 | DeVito |
| 6,006,124 A | 12/1999 | Fischell et al. |
| 6,016,449 A | 1/2000 | Fischell et al. |
| 6,018,682 A | 1/2000 | Rise |
| 6,024,700 A | 2/2000 | Nemirovski et al. |
| 6,024,702 A | 2/2000 | Iversen |
| 6,027,456 A | 2/2000 | Feler et al. |
| 6,038,477 A | 3/2000 | Kayyali |
| 6,044,292 A | 3/2000 | Heyrend et al. |
| 6,061,593 A | 5/2000 | Fischell et al. |
| 6,086,582 A | 7/2000 | Altman et al. |
| 6,091,015 A | 7/2000 | del Valle et al. |
| 6,092,058 A | 7/2000 | Smyth |
| 6,094,598 A | 7/2000 | Elsberry et al. |
| 6,113,553 A | 9/2000 | Chubbuck |
| 6,125,300 A | 9/2000 | Weijand et al. |
| 6,128,538 A | 10/2000 | Fischell et al. |
| 6,134,474 A | 10/2000 | Fischell et al. |
| 6,154,678 A | 11/2000 | Lauro |
| 6,161,045 A | 12/2000 | Fischell et al. |
| 6,163,725 A | 12/2000 | Peckham et al. |
| 6,164,284 A | 12/2000 | Schulman et al. |
| 6,169,981 B1 | 1/2001 | Werbos |
| 6,171,239 B1 | 1/2001 | Humphrey |
| 6,175,762 B1 | 1/2001 | Kirkup et al. |
| 6,181,965 B1 | 1/2001 | Loeb et al. |
| 6,185,455 B1 | 2/2001 | Loeb et al. |
| 6,216,045 B1 | 4/2001 | Black et al. |
| 6,224,549 B1 | 5/2001 | Drongelen |
| 6,240,315 B1 | 5/2001 | Mo et al. |
| 6,254,536 B1 | 7/2001 | DeVito |
| 6,263,237 B1 | 7/2001 | Rise |
| 6,280,394 B1 | 8/2001 | Maloney et al. |
| 6,304,775 B1 | 10/2001 | Iasemidis et al. |
| 6,309,410 B1 | 10/2001 | Kuzma et al. |
| 6,313,093 B1 | 11/2001 | Frey, II |
| 6,319,241 B1 | 11/2001 | King et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,358,202 B1 | 3/2002 | Arent |
| 6,360,122 B1 | 3/2002 | Fischell et al. |
| 6,366,813 B1 | 4/2002 | DiLorenzo |
| 6,427,086 B1 | 7/2002 | Fischell et al. |
| 6,436,708 B1 | 8/2002 | Leone et al. |
| 6,454,708 B1 | 9/2002 | Ferguson et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,549,804 B1 | 4/2003 | Osorio et al. |
| 6,577,893 B1 | 6/2003 | Besson et al. |
| 6,620,415 B2 | 9/2003 | Donovan |
| 6,658,287 B1 | 12/2003 | Litt et al. |
| 6,731,964 B2 | 5/2004 | Shenoy et al. |
| 6,821,233 B1 | 11/2004 | Colombo et al. |
| 6,966,882 B2 | 11/2005 | Horst |
| 7,010,351 B2 | 3/2006 | Firlik et al. |
| 7,011,605 B2 | 3/2006 | Shields |
| 7,162,305 B2 | 1/2007 | Tong et al. |
| 7,206,632 B2 | 4/2007 | King |
| 7,212,851 B2 | 5/2007 | Donoghue et al. |
| 7,280,870 B2 | 10/2007 | Nurmikko et al. |
| 7,346,396 B2 | 3/2008 | Barriskill et al. |
| 7,381,192 B2 | 6/2008 | Brodard et al. |
| 7,392,079 B2 | 6/2008 | Donoghue et al. |
| 7,647,097 B2 | 1/2010 | Flaherty et al. |
| 7,751,877 B2 | 7/2010 | Flaherty et al. |
| 2001/0023368 A1 | 9/2001 | Black et al. |
| 2001/0027336 A1 | 10/2001 | Gielen et al. |
| 2001/0029391 A1 | 10/2001 | Gluckman et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0016638 A1 | 2/2002 | Mitra et al. |
| 2002/0077534 A1 | 6/2002 | DuRousseau |
| 2002/0077620 A1 | 6/2002 | Sweeney et al. |
| 2002/0082514 A1 | 6/2002 | Williams et al. |
| 2002/0099412 A1 | 7/2002 | Fischell et al. |
| 2002/0169485 A1 | 11/2002 | Pless et al. |
| 2003/0004428 A1 | 1/2003 | Pless et al. |
| 2003/0050569 A1 | 3/2003 | Shenoy et al. |
| 2003/0074032 A1 | 4/2003 | Gliner |
| 2003/0082507 A1 | 5/2003 | Stypulkowski |
| 2003/0083716 A1 | 5/2003 | Nicolelis et al. |
| 2003/0083724 A1 | 5/2003 | Jog et al. |
| 2003/0093129 A1 | 5/2003 | Nicolelis et al. |
| 2003/0139782 A1 | 7/2003 | Duncan et al. |
| 2003/0139783 A1 | 7/2003 | Kilgore et al. |
| 2003/0149678 A1 | 8/2003 | Cook |
| 2003/0158587 A1 | 8/2003 | Esteller et al. |
| 2004/0006264 A1 | 1/2004 | Majarradi et al. |
| 2004/0068204 A1 | 4/2004 | Imran et al. |
| 2004/0133118 A1 | 7/2004 | Llinas |
| 2004/0138579 A1 | 7/2004 | Deadwyler et al. |
| 2005/0090756 A1 | 4/2005 | Wolf et al. |
| 2005/0137652 A1 | 6/2005 | Cauller et al. |
| 2005/0182341 A1 | 8/2005 | Katayama et al. |
| 2005/0273890 A1 | 12/2005 | Flaherty et al. |
| 2006/0029912 A1 | 2/2006 | Kearby et al. |
| 2006/0049957 A1 | 3/2006 | Surgenor et al. |
| 2006/0058627 A1 | 3/2006 | Flaherty et al. |
| 2006/0149338 A1 | 7/2006 | Flaherty et al. |
| 2006/0167371 A1 | 7/2006 | Flaherty et al. |
| 2006/0167530 A1 | 7/2006 | Flaherty et al. |
| 2006/0167564 A1* | 7/2006 | Flaherty et al. ............... 623/57 |
| 2006/0173259 A1 | 8/2006 | Flaherty et al. |
| 2006/0189900 A1 | 8/2006 | Flaherty |
| 2006/0195042 A1 | 8/2006 | Flaherty |
| 2006/0206167 A1 | 9/2006 | Flaherty et al. |

| | | | |
|---|---|---|---|
| 2006/0241356 | A1 | 10/2006 | Flaherty |
| 2006/0253166 | A1 | 11/2006 | Flaherty et al. |
| 2007/0032738 | A1 | 2/2007 | Flaherty et al. |
| 2007/0156126 | A1 | 7/2007 | Flaherty |
| 2010/0023021 | A1 | 1/2010 | Flaherty |
| 2010/0063411 | A1 | 3/2010 | Donoghue et al. |

FOREIGN PATENT DOCUMENTS

| | | |
|---|---|---|
| WO | WO 01/43635 | 6/2001 |
| WO | WO 01/60445 | 8/2001 |
| WO | WO 01/78833 | 10/2001 |
| WO | WO 01/93756 A2 | 12/2001 |
| WO | WO 02/093312 A2 | 11/2002 |
| WO | WO 02/100267 A1 | 12/2002 |
| WO | WO 03/026739 | 4/2003 |
| WO | WO 03/035165 | 5/2003 |
| WO | WO 03/037231 | 5/2003 |
| WO | WO 03/061465 A2 | 7/2003 |
| WO | WO 2006/044793 A2 | 4/2006 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B—Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electroencephalorophy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. ½, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al, "Neuronal Interactions Improve Cortical Population Coding of Movement Direction," The journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure for Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter," Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroprosthesis Suitable for Implantation Into the Brain," IEEE Transactions on Neural Systems and Rehabilitation Engineering, vol. 11, No. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering, vol. 3, No. 4, Dec. 1995.

Ferdinando Mussa-Ivaldi et al., "Brain-machine interfaces: computational demands and clinical needs meet basic neuroscience," Trends in Neurosciences, vol. 26, No. 6, Jun. 2003, pp. 329-334.

D.N. Harvey et al., "Multiple-Output Electromyographic Switching System," 1978 ISA, Pittsburgh, PA, 1978, pp. 121-123.

Faisal Karmali et al.," Environmental Control by a Brain-Computer Interface," Proceedings of the $22^{nd}$ Annual EMBS Int'l Conf., Jul. 23-28, 2000, Chicago, IL, pp. 2990-2992.

Alex Mihailidis et al. "Using artificial intelligence to assist people with dementia to be more independent," Proceedings of the $22^{nd}$ Annual EMBS Int'l Conf., Jul. 23-28, 2000, Chicago, IL, pp. 2993-2996.

* cited by examiner

BIOLOGICAL INTERFACE SYSTEM WITH GATED CONTROL SIGNAL

This application claims the benefit of priority under 35 U.S.C. §119(e) of U.S. provisional application No. 60/642,199, filed Jan. 6, 2005.

FIELD OF THE INVENTION

The present invention relates to medical devices and, more particularly, biological interface systems that include one or more devices controllable by processed multicellular signals of a patient. A processing unit produces a control signal based on multicellular signals received from a sensor comprising multiple electrodes. More particularly, the system includes a monitoring unit that monitors one or more system parameters and a gate that determines the status of the control signal.

DESCRIPTION OF RELATED ART

Biological interface devices, for example neural interface devices, are currently under development for numerous patient applications including restoration of lost function due to traumatic injury or neurological disease. Sensors, such as electrode arrays, implanted in the higher brain regions that control voluntary movement, can be activated voluntarily to generate electrical signals that can be processed by a biological interface device to create a thought invoked control signal. Such control signals can be used to control numerous devices including computers and communication devices, external prostheses, such as an artificial arm or functional electrical stimulation of paralyzed muscles, as well as robots and other remote control devices. Patients afflicted with amyotrophic lateral sclerosis (Lou Gehrig's Disease), particularly those in advanced stages of the disease, would also be appropriate for receiving a neural interface device, even if just to improve communication to the external world, including Internet access, and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information or other neural data, such as electrocorticogram (ECOG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression will be to more sophisticated human applications, such as those types of devices regulated by various governmental regulatory agencies including the Food and Drug Administration in the United States.

As sophisticated biological interface systems are approved by the FDA and become commercially available, these systems need to include numerous safety features required of medical devices. It will also be required that the systems safely control various devices, especially devices that, if improperly controlled, could potentially harm the patient or other individuals, such devices including wheelchairs, prosthetic limbs and robotic arms. These systems must be self-monitoring and handle malfunctions in a reliable manner to prevent injury. Simplified handling of the malfunction, as well as convenience and flexibility to the patient, their caregivers and family members will also be a requirement. There is therefore a need for an improved biological interface system which includes a sophisticated malfunction or potential malfunction handling system.

SUMMARY OF THE INVENTION

According to one exemplary aspect of the invention, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals. Another component of the system generates an alternate signal. A signal gate receives the processed signal and the alternate signal. The system further includes a monitoring unit that receives one or more pieces of system data and processes that system data to produce a system status signal transmitted to the signal gate. The signal gate transmit a control signal to a controllable device, the control signal comprising either the processed signal of the processing unit or the alternate signal, as determined by the system status signal transmitted by the monitoring unit.

In some exemplary embodiments, the monitoring unit compares system data or a derivative of system data to a threshold value, such as an adjustable threshold value. The monitoring unit processing is used to determine an unsafe or otherwise inappropriate, including a potentially problematic condition, when the processing unit should not be generating a control signal based on the multicellular signals of the patient. Examples of system configuration parameters that may be monitored by the monitoring unit include: noise level on system wiring; communication errors encountered; improper environmental conditions such as unacceptable electromagnetic fields encountered; a patient parameter outside of a target range; a controlled device parameter such as a parameter monitored by a sensor at an unacceptable level; detection of a computer virus; detection of an improper cable attachment; and other similar indicators of a potential system issue.

The alternate signal may cause the controlled device to enter a safe state or configuration, or may simply comprise a null signal that results in a stoppage in device control. In another preferred embodiment, the signal gate transmits processed signals to multiple controlled devices, and the system may include multiple alternative signals. In an alternative embodiment, the system includes multiple alternate signals than may be sent to a single controlled device, such as sending a first alternate signal when the monitoring unit detects the system in a first condition, and sending a second alternate signal when the monitoring unit detects the system in a second condition, such as a more severe condition than the first condition. Once the signal gate switches from sending the processed signal to the controlled device to sending the alternate signal, when the condition detected by the monitoring unit by processing the system data is at an unacceptable level, the controlled device will again receive the processed signals when the condition reverses itself back to an acceptable level. In an alternative embodiment, the signal gate latches, such that the alternate signal continues to be transmitted to the controlled device until a separate action, such as a system reset function, is activated. In another preferred embodiment, the system further includes an alarm assembly, such that the alarm assembly performs a function when the signal gate changes from transmitting the processed signal to transmitting an alternate signal. The function of the alarm assembly may be to sound an alarm transducer and/or dial a predetermined phone number and broadcast a prerecorded message.

According to another exemplary aspect, a method of producing a control signal for use in a biological interface system may be provided. The method may comprise: detecting multicellular signals emanating from one or more living cells of a patient; processing the detected multicellular signals to produce a processed signal; generating an alternative signal; providing a signal gate configured to receive the processed signal and the alternative signal, the signal gate selectively transmitting either the processed signal or the alternative signal to a controlled device as a control signal. The method may further comprise monitoring status of a biological interface system and producing a system status signal, and determining, based on the system status signal, which of the processed signal and the alternative signal is to be transmitted to the control signal.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings.

DESCRIPTION OF THE EMBODIMENTS

Figure 1:
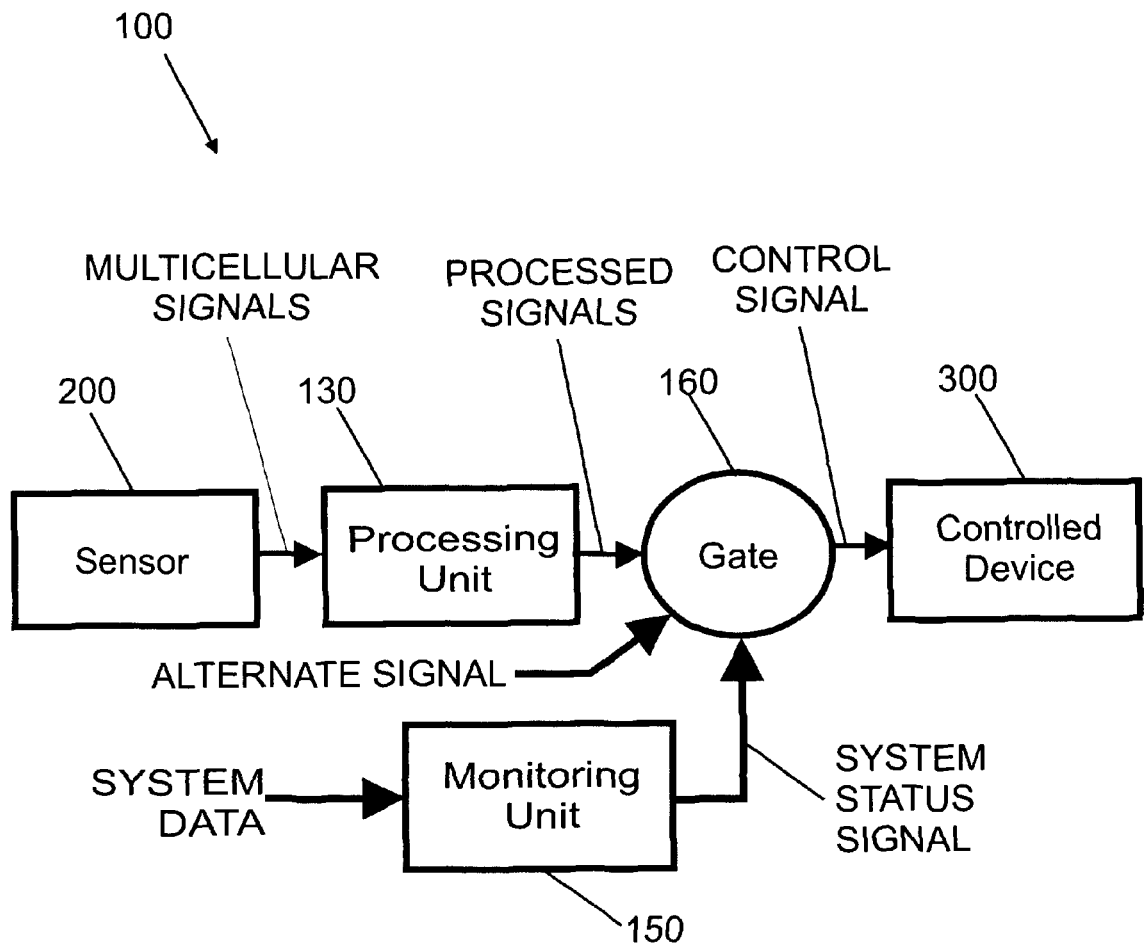
FIG. 1 illustrates a schematic representation of an exemplary embodiment of a biological interface system consistent with the present invention.

To facilitate an understanding of the invention, a number of terms are defined immediately herebelow.

Definitions

As used herein, the term "biological interface system" refers to a neural interface system or any system that interfaces with living cells that produce electrical activity or cells that produce other types of detectable signals.

The term "cellular signals," as used herein, refers to signals or combination of signals that may emanate from any living cell, such as, for example, subcellular signals, intracellular signals, and extracellular signals. For example, "cellular signals" may include, but not be limited to: neural signals (e.g., neuron action potentials or spikes, local field potential (LFP) signals, electroencephalogram (EEG) signals, electrocorticogram signals (ECoG), and signals whose frequency range falls between single neuron spikes and EEG signals); cardiac signals (e.g., cardiac action potentials); electromyogram (EMG) signals; glial cell signals; stomach cell signals; kidney cell signals; liver cell signals; pancreas cell signals; osteocyte cell signals; sensory organ cell signals (e.g., signals emanating from the eye or inner ear); tumor cell signals; and tooth cell signals.

The term "multicellular signals," as used herein, refers to signals emanating from two or more cells, or multiple signals emanating from a single cell. The term "subcellular signals," as used herein, refers to, for example, a signal derived from a part of a cell, a signal derived from one particular physical location along or within a cell, a signal from a cell extension (e.g., dendrite, dendrite branch, dendrite tree, axon, axon tree, axon branch, pseudopod, or growth cone), and signals from organelles (e.g., golgi apparatus or endoplasmic reticulum). The term "intracellular signals," as used herein, refers to a signal that is generated within a cell or by the entire cell that is confined to the inside of the cell up to and including the membrane. The term "extracellular signals," as used herein, refers to signals generated by one or more cells that occur outside of the cell(s).

As used herein, the term "patient" refers to any animal, such as a mammal and preferably a human. Specific examples of a "patient" include, but are not limited to: individuals requiring medical assistance; healthy individuals; individuals with limited function; and individuals with lost motor or other function due to traumatic injury or neurological disease.

As used herein, the term "configuration" refers to any alteration, improvement, repair, calibration, or other system modifying event whether manual in nature or partially or fully automated. The term "configuration parameter," as used herein, refers to a variable, or a value of the variable, of a component, device, apparatus, and/or system. A configuration parameter has a value that can be: set or modified; used to perform a function; used in a mathematical or other algorithm; used as a threshold value to perform a comparison; and any combinations thereof. A configuration parameter's value determines the characteristics or behavior of something. System configuration parameters are variables of the system of the present invention, such as those used to by the processing unit to produce processed signals.

Other, numerous subsets of configuration parameters are applicable, these subsets including but not limited to: calibration parameters such as a calibration frequency parameter;

controlled device parameters such as a time constant parameter; processing unit parameters such as a cell selection criteria parameter; patient parameters such as a patient physiologic parameter such as heart rate; multicellular signal sensor parameters; other sensor parameters; system environment parameters; mathematical algorithm parameters; a safety parameter; and other parameters. Certain parameters may be controlled by the patient's clinician, such as a password-controlled parameter securely controlled by an integral permission routine of the system. Certain parameters may represent a "threshold" such as a success threshold used in a comparison to determine if the outcome of an event was successful. In numerous steps of a system configuration or other function, a minimum performance or other measure may be maintained by comparing a detected signal, or the output of an analysis of one or more signals, to a success threshold.

As used herein, the term "discrete component" refers to a component of a system such as those defined by a housing or other enclosed or partially enclosed structure, or those defined as being detached or detachable from another discrete component. Each discrete component can transmit information to a separate component through the use of a physical cable, including one or more of electrically conductive wires or optical fibers, or transmission of information can be accomplished wirelessly. Wireless communication can be accomplished with a transceiver that may transmit and receive data such as through the use of "Bluetooth" technology or according to any other type of wireless communication means, method, protocol or standard, including, for example, code division multiple access (CDMA), wireless application protocol (WAP), Infrared or other optical telemetry, radio frequency or other electromagnetic telemetry, ultrasonic telemetry or other telemetric technologies.

As used herein, the term "routine" refers to an established function, operation, or procedure of a system, such as an embedded software module that is performed or is available to be performed by the system. Routines may be activated manually such as by an operator of a system, or occur automatically such as a routine whose initiation is triggered by another function, an elapsed time or time of day, or other trigger. The devices, apparatus, systems and methods of the present invention may include or otherwise have integrated into one or their components, numerous types and forms of routines. An "adaptive processing routine" is activated to determine and/or cause a routine or other function to be modified or otherwise adapt to maintain or improve performance. A competitive routine is activated to provide a competitive function for the patient of the present invention to compete with, such as a function which allows an operator of the system to compete with the patient in a patient training task; or an automated system function which controls a visual object which competes with a patient controlled object. A "configuration routine" is activated to configure one or more system configuration parameters of the system, such as a parameter that needs an initial value assigned or a parameter that needs an existing parameter modified.

A system "diagnostic routine" is activated, automatically or with operator intervention, to check one or more functions of the system to insure proper performance and indicate acceptable system status to one or more components of the system or an operator of the system. A "language selection routine" is activated to change a language displayed in text form on a display and/or in audible form from a speaker. A "patient training routine" is activated to train the patient in the use of the system and/or train the system in the specifics of the patient, such as the specifics of the patient's multicellular signals that can be generated by the patient and detected by the sensor. A "permission routine" is activated when a system configuration or other parameter is to be initially set or modified in a secured manner. The permission routine may use one or more of: a password; a restricted user logon function; a user ID; an electronic key; a electromechanical key; a mechanical key; a specific Internet IP address; and other means of confirming the identify of one or more operators prior to allowing a secure operation to occur. A "remote technician routine" is activated to allow an operator to access the system of the present invention, or an associated device, from a location remote from the patient, or a system component to be modified. A "system configuration routine" is activated to configure the system, or one or more components or associated devices of the system. In a system configuration routine, one or more system configuration parameters may be modified or initially set to a value. A "system reset routine" is activated to reset the entire system or a system function. Resetting the system is sometimes required with computers and computer based devices such as during a power failure or a system malfunction.

General Description of the Embodiments

Systems, methods, and devices consistent with the invention detect cellular signals generated within a patient's body and implement various signal processing techniques to generate processed signals for transmission to one or more devices to be controlled. The system includes a sensor comprising a plurality of electrodes that detect multicellular signals from one or more living cells, such as from the central or peripheral nervous system of a patient. The system further includes a processing unit that receives and processes the multicellular signals and transmits a processed signal to a controlled device. The processing unit utilizes various electronic, mathematic, neural net, and other signal processing techniques in producing the processed signal.

The system further includes a monitoring unit that receives and monitors one or more pieces of system data, such as values of one or more system configuration parameters. The monitoring unit contains processing functions to determine if the data represents a condition in which it is preferably that the controlled device not receive the intended processed signals from the processing unit. The monitoring unit may compare the data or a derivative of the data, such as a mathematical derivative of the data, to a threshold value maintained in memory of the system. The system further includes a control gate that receives the processed signal from the processing unit as well as an alternative signal generated by the system. The control gate receives a system status signal from the monitoring unit, where the system status signal determines whether the gate sends the processed signal or the alternative signal to the controlled device.

Detailed Description of the Embodiments

Reference will now be made in detail to the present embodiments of the invention, examples of which are illustrated in the accompanying drawings. Wherever possible, the same reference numbers will be used throughout the drawings to refer to the same or like parts.

FIG. 1 illustrates a schematic representation of a biological interface system 100 that comprises a signal control gate 160 used to send a specific type of signal to a controlled device 300. System 100 may comprise multiple system components including controlled device 300 as well as components used to create a control signal for controlled device 300. Sensor 200 includes multiple electrodes, each configured to detect one or more cellular signals. Sensor 200 may be implanted in the patient or at a location proximate the patient, such as on the patient's skull. Sensor 200 may be a single discrete component. Alternatively, sensor 200 may comprise multiple components, such as an array assembly implanted in the brain of the patient and one or more electrodes in proximity to a peripheral nerve. Numerous types and configurations of sensors of the present invention are described in detail in reference to subsequent figures herebelow.

Sensor 200 is attached to processing unit 130 via, for example, electrical wires. Processing unit 130 may also comprise a single discrete component or multiple components, such as implanted or partially implanted components or components external to the patient's body. Processing unit 130 receives the multicellular signals from sensor 200 and processes the multicellular signals to produce a signal that can be used to control controlled device 300. These processed signals can control multiple controlled devices, simultaneously or independently. The processed signals are sent to the signal control gate 160 with a wired connection, such as an electrical wire or optical fiber connection, or via wireless transmission such as RF transmissions. In systems that have processing units 130 comprising multiple discrete components, such as a configuration with a fully implanted processing unit first portion and an external processing unit second portion, data is transmitted between the first portion and the second portion via, for example, infrared wireless transmissions including an infrared photodiode on the implanted device and an infrared receiving phototransistor on the external portion. Signal control gate 160 includes electronic components, such as a solid state relay, to accept the processed signals and alternate signal as inputs and electronically select one of the inputs for transmission to the controlled device.

An alternate signal, generated by one or more components of the system such as processing unit 130, is also sent to gate 160 via wired or wireless transmission. The alternate signal is chosen such that if the system produces unacceptable processed signals, the alternate signal avoids patient injury or other adverse events. The alternate signal may be a signal void of controlled device control instructions such as a null signal. The alternate signal may cause the controlled device to enter a safe mode, such as a wheelchair with locked wheels, or an exoskeleton that places the patient's hand in a position to protect the patient's face. The alternate signal may be a derivative of the processed signal such as a signal that causes a vehicle to operate, but at reduced speed, or a signal that controls a prosthetic limb, but with limited applied forces. The alternate signal is sent to controlled device 300 when signal control gate 160 receives a specific command from monitoring unit 150 in the form of a system status signal. The system status signal has two states: (1) one that causes signal gate 160 to transmit the processed signal; and (2) one that causes signal gate 160 to transmit the alternative signal.

When the system data is indicative of acceptable system conditions, the system status signal state causes signal gate 160 to transmit the processed signals. When an unacceptable condition of the system is subsequently detected by an analysis of the system data, the system status signal causes the alternative signal to be transmitted. In one preferred embodiment, signal gate 160 latches to continue to transmit the alternative signal regardless of any system data changes. In an alternative embodiment, signal gate 60 can switch back to transmitting the processed signal when the system data returns to an acceptable condition, as determined by monitoring unit 150. In another alternative embodiment, the system status signal includes three or more states, and signal gate 160 can send a second alternate signal or perform a third or fourth function when the third or forth states of the system status signal is received.

In an exemplary embodiment, the system status signal includes multiple pieces of data such as a command to an alarm assembly, not shown, that alerts the patient, or other person such as a family member at a remote location, that the processed signal is no longer controlling the controlled device. In another exemplary embodiment, signal gate 160 includes a latching function, such that if the condition of the system data which triggered signal gate 160 to no longer transmit the processed signal reverses back to a previously acceptable state of the same system data, the alternate signals remains as the signal transmitted to the controlled device. When signal gate 160 is latched such that the alternate signal is being transmitted to the controlled device, an operator intervention may be required to unlatch signal gate 160. A reset function may be used to again transmit the processed signals to the controlled device 300. In an embodiment, the system includes a system diagnostic routine, and a confirmed system acceptable status must be received prior to the processed signals being transmitted by gate 160 to controlled device 300. In an alternative embodiment, when the condition causing the alternate signal to be transmitted is reversed, gate 160 again begins to transmit the processed signal to the controlled device, such as without patient or other operator intervention.

Monitoring unit 150 receives the system data from one or more components of the system or an external device such as a sensor monitoring the system's environment. The system data of the present invention may include one or more system configuration parameters. The system data may include the multicellular signals or a derivative of these signals. The system data is processed by monitoring unit 150 and the results of the processing or analysis is used to generate the system status signal which is used by signal gate 160 to send, either the processed signal of processing unit 130 or the alternate signal generated by the system, to controlled device 300. In an embodiment, monitoring unit 150 performs a correlation of two system configuration parameters such as patient consciousness and a multicellular signal parameter. In cases where the patient is asleep, if a multicellular signal were causing a controlled vehicle to move, monitoring unit 150 would send a system status signal preventing any motion of the vehicle.

Monitoring unit 150 may receive multiple pieces of system data and may perform many different forms of processing or analysis such as a mathematical analysis including a comparison to a threshold value. The threshold value may be adjustable, such as by a clinician at location remote from the patient utilizing the Internet and a system permission routine that prevents unauthorized access to the system. The processing of monitoring unit 150 is configured to detect an unacceptable condition, or a potentially unacceptable condition for sending the processed signals to the controlled device 300. Upon detection of an unacceptable condition or state of the system, monitoring unit 150 sends a system status signal that causes signal gate 160 to stop sending the processed signal of processing unit 130 and begin to send the alternate signal of the system. Depending on the type of controlled device, the alternate signal may be a null signal, or a signal that causes the controlled device to enter a pre-determined safe state.

Monitoring unit 150 can monitor multiple system configuration parameters in order to determine an unacceptable condition. In an embodiment, the system includes multiple wires such as bundled wires or ribbon cables of wires. Monitoring unit 150 may monitor cross-talk in one or more wires, and compare to a cross-talk threshold value to determine an unacceptable condition. Monitoring unit 150 may measure impedance in one or more wires and/or electrodes of the system, and an unacceptable condition may be identified when the impedance is above or below a threshold value. Other types of data can be compared to a threshold value, such as a safety level parameter that is stored in processing unit 130. Monitoring unit 150 may monitor the processed signal, and measure one or more characteristics such as signal noise. The processed signal can be monitored, such as a processed signal that controls one or more of the following properties of a controlled device or portion of a controlled device: position; velocity; acceleration; torque; and force. The components of the system may transmit data from component to component using wired or wireless means. In a preferred embodiment, monitoring unit 150 monitors communication errors in data transmissions between components, and an unacceptable condition is triggered by a type of error detected and/or a quantity of errors detected.

Figure 2:
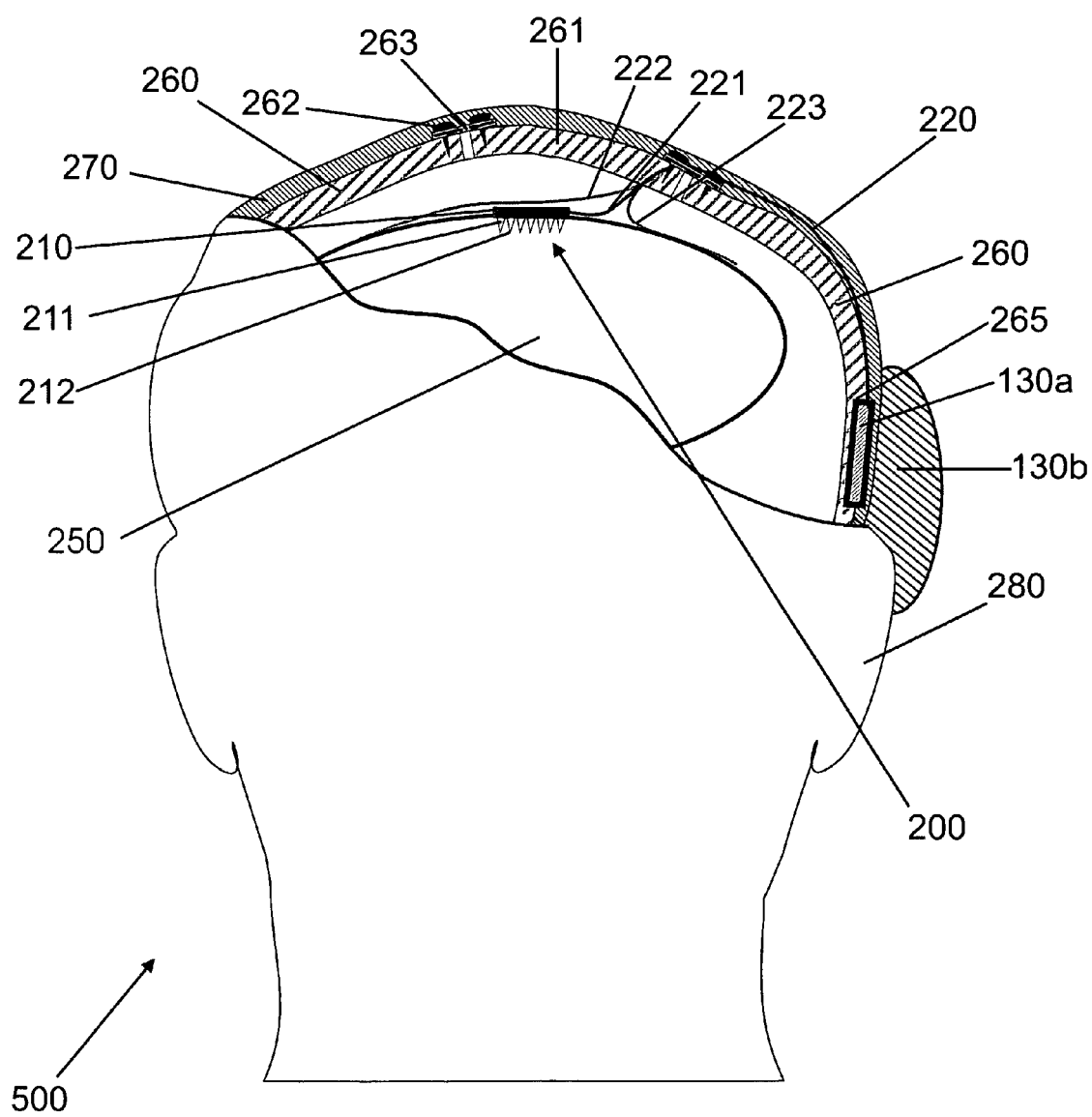
FIG. 2 illustrates an exemplary embodiment of a portion of the biological interface system consistent with the present invention, wherein sensor electrodes are implanted in the brain of a patient and a portion of a processing unit is implanted on the skull of the patient.

Referring now to FIG. 2, a brain implant apparatus consistent with an embodiment of the present invention is illustrated. As shown in FIG. 2, the system includes an array of electrodes assembly (e.g., sensor 200), which has been inserted into a brain 250 of patient 500, through a previously created opening in scalp 270 and skull 260 in a surgical procedure known as a craniotomy. Sensor 200 includes a plurality of longitudinal projections 211 extending from a base (e.g., array substrate 210). Projections 211 may be rigid, semi-flexible or flexible, the flexibility such that each projection 211 can still penetrate into neural tissue, potentially with an assisting device or with projections that only temporarily exist in a rigid condition. Sensor 200 has been inserted into brain 250, preferably using a rapid insertion tool, such that the projections 211 pierce into brain 250 and sensor substrate 210 remains in close proximity to or in light contact with the surface of brain 250. At the end of each projection 211 is an electrode 212. In alternative embodiments, electrodes can be located at a location other than the tip of projections 211 or multiple electrodes may be included along the length of one or more of the projections 211. One or more projections 211 may be void of any electrode, such projections potentially including anchoring means such as bulbous tips or barbs.

Electrodes 212 are configured to detect electrical brain signals or impulses, such as individual neuron spikes or signals that represent clusters of neurons such as local field potential (LFP) and electroencephalogram (EEG) signals. Each electrode 212 may be used to individually detect the firing of multiple neurons, separated by neuron spike discrimination techniques. Other applicable signals include electrocorticogram (ECOG) signals and other signals, such as signals between single neuron spikes and EEG signals. Sensor 200 may be placed in any location of a patient's brain allowing for electrodes 212 to detect these brain signals or impulses. In a preferred embodiment, electrodes 212 can be inserted into a part of brain 250 such as the cerebral cortex. Alternative forms of penetrating electrodes, such as wire or wire bundle electrodes, can make up or be a component of the sensor of the present invention. In addition to or alternative from neural signals, the system of the present invention may utilize other types of cellular signals to produce a processed signal to control a device. The various forms of penetrating electrodes described above can be placed into tissue within or outside of the patient's cranium, such tissue including but not limited to: nerve tissue such as peripheral nerve tissue or nerves of the spine; organ tissue such as heart, pancreas, liver or kidney tissue; tumor tissue such as brain tumor or breast tumor tissue; other tissue and any combination thereof.

Alternatively or additionally, the sensor of the present invention may employ non-penetrating electrode configurations, not shown, such as subdural grids placed inside the cranium such as to record LFP signals. In addition to subdural grids, the sensor may comprise other forms of non-penetrating electrodes such as flat electrodes, coil electrodes, cuff electrodes and skin electrodes such as scalp electrodes. These non-penetrating electrode configurations are placed in, on, near or otherwise in proximity to the cells whose signals are to be detected, such as neural or other cellular signals. In another alternative embodiment, the sensor of the present invention includes detectors other than electrodes, such as photodetectors that detect cellular signals represented by a light emission. The light emission can be caused by a photodiode, integrated into the sensor or other implanted or non-implanted system component, shining one or more wavelengths of light on the appropriate cells. In addition to the numerous types of cells described above, one or more of the various configurations of the sensor of the present invention may utilize any living cell of the body that emanates cellular signals. In a preferred embodiment, the cellular signals are under voluntary control of the patient.

Although FIG. 2 depicts sensor 200 as a single discrete component, in alternative embodiments the sensor may comprise multiple discrete components, including one or more types of electrodes or other cellular signal detecting elements, each configured and placed to detect similar or dissimilar types of cellular signals. Multiple sensor discrete components can be implanted entirely within: the skull, an extracranial location such as a peripheral nerve, or external to the body; or the components can be placed in any combination of these locations.

Sensor 200 serves as the multicellular signal sensor of the biological interface system of the present invention. While FIG. 2 shows sensor 200 as eight projections 211 with eight electrodes 212, sensor 200 may include one or more projections with and without electrodes, both the projections and electrodes having a variety of sizes, lengths, shapes, surface areas, forms, and arrangements. Moreover, sensor 200 may be a linear array (e.g., a row of electrodes) or a two-dimensional array (e.g., a matrix of rows and columns of electrodes such as a ten by ten array), or wire or wire bundle electrodes. An individual wire lead may include a plurality of electrodes along its length. Projections and electrodes may have the same materials of construction and geometry, or there may be varied materials and/or geometries used in one or more electrodes. Each projection 211 and electrode 212 of FIG. 2 extends into brain 250 to detect one or more cellular signals such as those generated from the neurons located in proximity to each electrode 212's placement within the brain. Neurons may generate such signals when, for example, the brain instructs a particular limb to move in a particular way and/or the brain is planning that movement. In a preferred embodiment, the electrodes reside within the arm, hand, leg or foot portion of the motor cortex of the brain. The processing unit of the present invention may assign one or more specific cellular signals to a specific use, such as a specific use correlated to a patient imagined event. In a preferred embodiment, the one or more cellular signals assigned to a specific use are under voluntary control of the patient.

Referring back to FIG. 2, the processing unit of the present invention includes processing unit first portion 130a, placed under scalp 270 at a location near patient 500's ear 280. Processing unit first portion 130a receives cellular signals from sensor 200 via wire bundle 220 (e.g., a multi-conductor cable). In a preferred embodiment, wire bundle 220 includes a conductor for each electrode 212. Processed signals are produced by processing unit first portion 130a and other processing unit discrete components, such as processing unit second portion 130b removably placed on the external skin surface of patient 500 near ear 280. Processing unit second portion 130b remains in relative close proximity to implanted component processing unit first portion 130a through one or more fixation means such as cooperative magnetic means in both components, or body attachment means such that the processing unit second portion 130b is attached to eye glasses, an ear wrapping arm, a hat, mechanical straps, or an adhesive pad. Processing unit first portion 130a and processing unit second portion 130b work in combination to receive multicellular signal data and create a time code of brain activity.

In the preferred embodiment depicted in FIG. 2, bone flap 261 (e.g., the original bone portion removed in the craniotomy) may be used to close the hole made in the skull 260 during the craniotomy, obviating the need for a prosthetic closure implant. Bone flap 261 is attached to skull 260 with one or more straps (e.g., bands 263), which preferably comprises titanium or stainless steel. Band 263 is secured to bone flap 261 and skull 260 with bone screws 262. Wire bundle 220 passes between bone flap 261 and the hole cut into skull 260. During the surgical procedure, bone recess 265 was made in skull 260 such that processing unit first portion 130a could be placed in the indentation, allowing scalp 270 to lie relatively flat and free of tension in the area proximal to processing unit first portion 130a. A long incision in scalp 270 between the craniotomy site and the recess 265 can be made to place processing unit first portion 130a in recess 265. Alternatively, an incision can be made to perform the craniotomy, and a separate incision made to form recess 265, after which the processing unit first portion 130a and wire bundle 220 can be tunneled under scalp 270 to the desired location. Processing unit first portion 130a is attached to skull 260 with one or more bone screws or a biocompatible adhesive.

In an alternative embodiment, processing unit first portion 130a may be placed entirely within skull 260 or be geometrically configured and surgically placed to fill the craniotomy hole instead of bone flap 261. Processing unit first portion 130a can be placed in close proximity to sensor 200, or a distance of 5-20 cm can separate the two components. Processing unit first portion 130a includes a biocompatible housing which creates a fluid seal around wire bundle 220 and numerous internal components of processing unit first portion 130a, internal components not shown. Internal components of Processing unit first portion 130a may provide one or more of the following functions: signal processing of the cellular signals received from sensor 200 such as buffering, amplification, digital conversion and multiplexing, wireless transmission of cellular signals, a partially processed, or derivative form of the cellular signals, or other data; inductive power receiving and conversion; and other functions well known to implanted electronic assemblies such as implanted pacemakers, defibrillators, and pumps.

Processing unit second portion 130b, removably placed at a location proximate to implanted processing unit first portion 130a, but external to patient 500, receives data from processing unit first portion 130a via wireless communication through the skin, such as infrared or radiofrequency wireless data transfer means. Processing unit second portion 130b includes, in addition to wireless data receiving means, wireless power transfer means such as an RF coil which inductively couples to an implanted coil, signal processing circuitry, an embedded power supply such as a battery, and data transfer means. The data transfer means of processing unit second portion 130b may be wired or wireless, and transfer data to one or more of: implanted processing unit first portion 130a; a different implanted device; and an external device such as an additional component of the processing unit of the present invention, a controlled device of the present invention or a computer device such as a configuration computer with Internet access.

Referring back to FIG. 2, electrodes 212 transfer the detected cellular signals to processing unit first portion 130a via array wires 221 and wire bundle 220. Wire bundle 220 includes multiple conductive elements and array wires 221, which preferably include a conductor for each electrode 212 of sensor 200. Also included in wire bundle 220 are two conductors: first reference wire 222 and second reference wire 223, each of which is placed in an area in relative proximity to sensor 200 such as on the surface of brain 250 near the insertion location. First reference wire 222 and second reference wire 223 may be redundant and provide reference signals used by one or more signal processing elements of the processing unit of the present invention to process the cellular signal data detected by one or more electrodes. In an alternative embodiment, not shown, sensor 200 may comprise multiple discrete components and multiple bundles of wires connect to one or more discrete components of the processing unit, such as processing unit first portion 130a. In another alternative embodiment, cellular signals detected by sensor 200 are transmitted to processing unit first portion 130a via wireless technologies, such as infrared communication incorporated into an electronic module of sensor 200. Such transmissions penetrate the skull of the patient, obviating the need for wire bundle 220, array wires 221, and any physical conduit passing through skull 260 after the surgical implantation procedure is completed.

Processing unit first portion 130a and processing unit second portion 130b independently or in combination preprocess the received cellular signals (e.g., impedance matching, noise filtering, or amplifying), digitize them, and further process the cellular signals to extract neural data that processing unit second portion 130b may then transmit to an external device, such as an additional processing unit component and/or any device to be controlled by the processed multicellular signals. For example, the external device may decode the received neural data into control signals for controlling a prosthetic limb or limb assist device or for controlling a computer cursor. In an alternative embodiment, the external device may analyze the neural data for a variety of other purposes. In another alternative embodiment, the device receiving transmissions from processing unit second portion 130b is an implanted device.

Processing unit first portion 130a and processing unit second portion 130b independently or in combination include signal processing circuitry to perform multiple signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controlled device. Processing unit first portion 130a and processing unit second portion 130b may include one or more components to assist in processing the multicellular signals or to perform additional functions. These components include but are not limited to: a temperature sensor; a pressure sensor; a strain gauge; an accelerometer; a volume sensor; an electrode; an array of electrodes; an audio transducer; a mechanical vibrator; a drug delivery device; a magnetic field generator; a photo detector element; a camera or other visualization apparatus; a wireless communication element; a light producing element; an electrical stimulator; a physiologic sensor; a heating element; and a cooling element.

Processing unit first portion 130a transmits raw or processed cellular signal data to processing unit second portion 130b through integrated wireless communication means, such as the infrared communication means of FIG. 2, or alternative means including but not limited to radiofrequency communications, other optical communications, inductive communications, ultrasound communications and microwave communications. In a preferred, alternate embodiment, processing unit first portion 130a includes both infrared communication means for short-range high baud rate communication, and radiofrequency communication means for longer range, lower baud rate communication. This wireless transfer allows sensor 200 and processing unit first portion 130a to be completely implanted under the skin of the patient, avoiding the need for implanted devices that require protrusion of a portion of the device or wired connections through the skin surface. In an alternative embodiment, a through the skin pedestal connector is utilized between either the implanted sensor 200 or processing unit first portion 130a and an external component. Processing unit first portion 130a includes a coil, not shown, which receives power through inductive coupling, on a continual or intermittent basis from an external power transmitting device such as processing unit second portion 130b. The inductive coupling power transfer configuration obviates the need for any permanent power supply, such as a battery, integral to processing unit first portion 130a.

In addition to or in place of power transmission, the integrated coil of processing unit first portion 130a and its associated circuitry may receive data from an external coil whose signal is modulated in correlation to a specific data signal. The power and data can be delivered to processing unit first portion 130a simultaneously such as through simple modulation schemes in the power transfer that are decoded into data for processing unit first portion 130a to use, store or facilitate another function. A second data transfer means, in addition to a wireless means such as an infrared LED, can be accomplished by modulating a signal in the coil of processing unit first portion 130a that data is transmitted from the implant to an external device including a coil and decoding elements. In a preferred embodiment, the processing unit first portion 130a includes an embedded ID, which can be wirelessly transmitted to the processing unit second portion 130b or a separate discrete component via the various wireless transmission means described above. In another preferred embodiment, processing unit second portion 130b includes means of confirming proper ID from processing unit first portion 130a, and processing unit second portion 130b also includes an embedded ID.

Processing unit first portion 130a and processing unit second portion 130b may independently or in combination conduct adaptive processing of the received cellular signals by changing one or more parameters of the system to achieve acceptable or improved performance. Examples of adaptive processing include, but are not limited to: changing a system configuration parameter during a system configuration; changing a method of encoding neural or other cellular signal data; changing the type, subset, or amount of cellular signal data that is processed; or changing a method of decoding neural or other cellular signal data. Changing an encoding method may include changing neuron spike sorting methodology, calculations, thresholds, or pattern recognition methodologies. Changing a decoding methodology may include changing variables, coefficients, algorithms, and/or filter selections. Other examples of adaptive processing may include changing over time the type or combination of types of signals processed, such as EEG, ECOG, LFP, neural spikes, or other cellular signal types.

Processing unit first portion 130a and processing unit second portion 130b may independently or in combination also transmit electrical signals to one or more electrodes 212 such as to stimulate, polarize, hyperpolarize or otherwise cause an effect on one or more cells of neighboring tissue. Specific electrodes may record cellular signals only, or deliver energy only, and specific electrodes may provide both functions. In an alternative embodiment, a separate device, not shown but preferably an implanted device with the ability to independently or in combination provide an electrical signal to multiple electrodes, delivers stimulating energy to one or more electrodes 212 or different electrodes. Stimulating electrodes in various locations can transmit signals to the central nervous system, peripheral nervous system, other body systems, body organs, muscles and other tissue or cells. The transmission of these signals is used to perform one or more functions including but not limited to: pain therapy; muscle stimulation; seizure disruption; stroke rehabilitation; coma recovery; and patient feedback.

In an alternative embodiment, processing unit first portion 130a and potentially additional signal processing functions are integrated into sensor 200, such as, for example, through the use of a bonded electronic microchip. In another alternative embodiment, processing unit first portion 130a may also receive non-neural cellular signals and/or other biologic signals, such as from an implanted sensor. These signals may be in addition to received neural multicellular signals, and they may include but are not limited to: EKG signals, respiration signals, blood pressure signals, electromyographic activity signals and glucose level signals. Such biological signals may be used to change the state of the biological interface system of the present invention or one of its discrete components. Such state changes include but are not limited to: turn system or component on or off; to begin a configuration routine; to initiate or conclude a step of a configuration or other routine; and to start or stop another system function. In another alternative embodiment, processing unit first portion 130a and processing unit second portion 130b independently or in combination produce one or more additional processed signals, to additionally control the controlled device of the present invention or to control one or more additional controlled devices.

In an alternative, preferred configuration of implanted components, a discrete component such as a sensor of the present invention is implanted within the cranium of the patient, such as sensor 200 of FIG. 2, a processing unit or a portion of the processing unit is implanted in the torso of the patient, and one or more discrete components are external to the body of the patient. The processing unit may receive multicellular signals from the sensor via wired (e.g., conductive wires and optic fibers) or wireless communication. The sensor 200 preferably includes signal processing means including signal processing up to and including digitizing the multicellular signals. In another alternative embodiment, for an acute (less than 24 hours) or sub-chronic (less than 30 days) application, for example, a through the skin, or transcutaneous device is used to transmit or enable the transmission of the multicellular signals and/or a derivative or preprocessed form of the multicellular signals.

Figure 3:
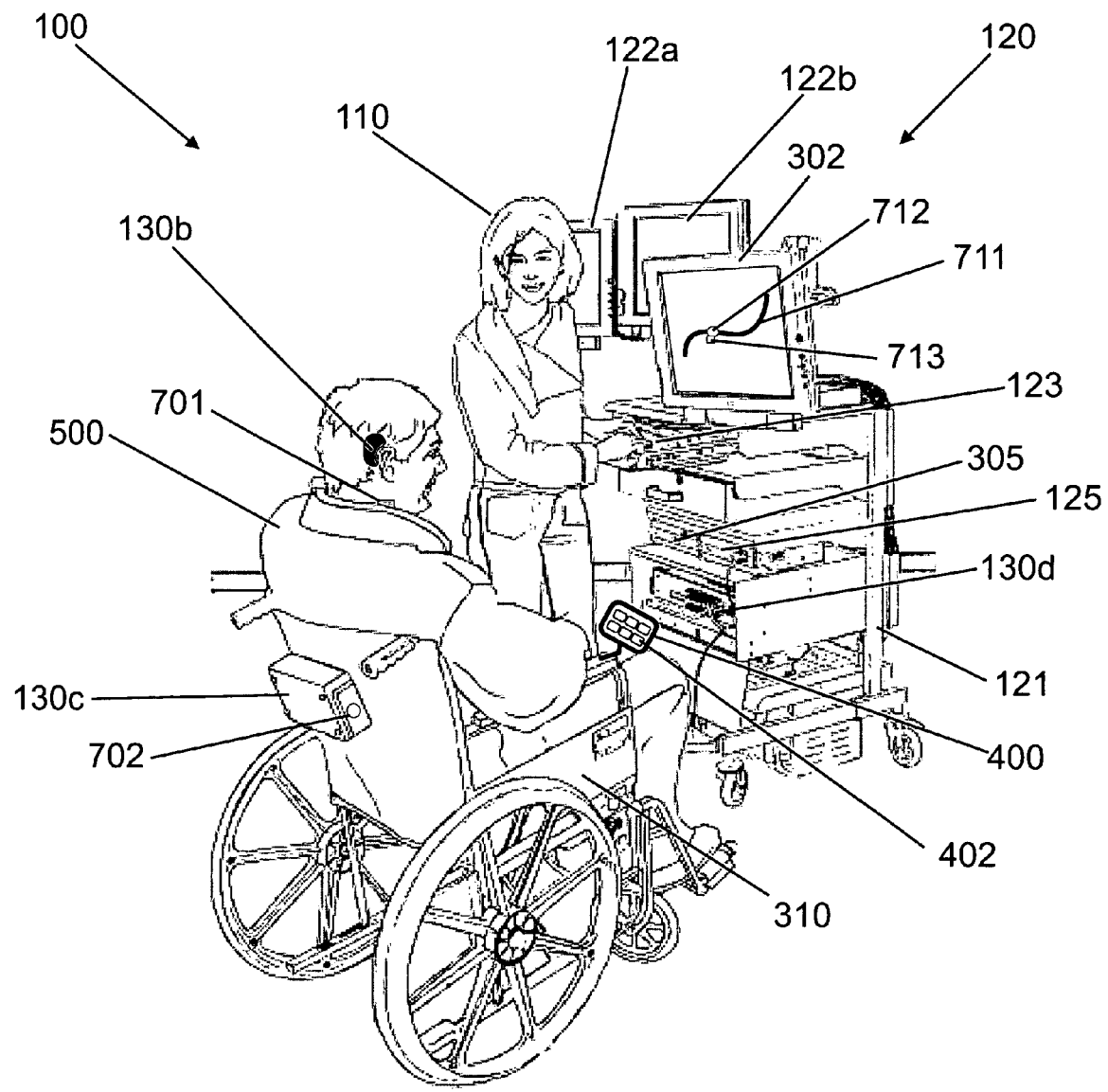
FIG. 3 illustrates another exemplary embodiment of a biological interface system consistent with the present invention, wherein an operator configures the system at the patient site.

As shown in FIG. 3, a biological interface system 100 may comprise implanted components (not shown) and components external to the body of a patient 500. A sensor for detecting multicellular signals, preferably a two dimensional array of multiple protruding electrodes, has been implanted in the brain of patient 500, in an area such as the motor cortex. In a preferred embodiment, the sensor is placed in an area to record multicellular signals that are under voluntary control of the patient. Alternatively or additionally to the two dimensional array, the sensor may include one or more wires or wire bundles which include a plurality of electrodes. Patient 500 of FIG. 3 is shown as a human being, but other mammals and life forms that produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device. Numerous types of patients, including healthy individuals, are applicable to the system of the present invention. The patient of the present invention may be a quadriplegic, a paraplegic, an amputee, a spinal cord injury victim, or an otherwise physically impaired person. Alternatively or in addition, patient 500 may have been diagnosed with one or more of: obesity, an eating disorder, a neurological disorder, a psychiatric disorder, a cardiovascular disorder, an endocrine disorder, sexual dysfunction, incontinence, a hearing disorder, a visual disorder, sleeping disorder, a movement disorder, a speech disorder, physical injury, migraine headaches, or chronic pain. System 100 can be used to treat one or more medical conditions of patient 500, or to restore, partially restore, replace or partially replace a lost function of patient 500.

Alternatively, system 100 can be utilized by patient 500 to enhance performance, such as, for example, if patient 500 did not have a disease or condition from which a therapy or restorative device could provide benefit, but did have an occupation wherein thought control of a device provided an otherwise unachieved advancement in healthcare, crisis management and national defense. Thought control of a device can be advantageous in numerous healthy individuals including but not limited to: a surgeon, such as an individual surgeon using thought control to maneuver three or more robotic arms in a complex laparoscopic procedure or a surgeon controlling various instruments at a location remote from the instruments and the surgical procedure; a crisis control expert, such as a person who in attempting to minimize death and injury uses thought control to communicate different pieces of data and/or control multiple pieces of equipment, such as urban search and rescue equipment, simultaneously during an event such as an earthquake or other disaster, both natural disasters and those caused by man; a member of a bomb squad, such as an expert who uses thoughts to control multiple robots and/or robotic arms to remotely diffuse a bomb; and military personnel who uses thought control to communicate with other personnel and control multiple pieces of defense equipment, such as artillery, aircraft, watercraft, land vehicles, and reconnaissance robots. It should be noted that the above advantages of system 100 to a healthy individual are also advantages achieved in a patient such as a quadriplegic or paraplegic. In other words, a quadriplegic could provide significant benefit to society, such as in controlling multiple bomb diffusing robots, in addition to his or her own ambulation and other quality of life devices. Patients undergoing implantation and use of the system 100 of the present invention may provide numerous occupational and other functions not available to individuals that do not have the biological interface system of the present invention.

The sensor electrodes of system 100 can be used to detect various multicellular signals as has been described in detail in reference to FIG. 2 hereabove. The sensor is connected via a multi-conductor cable, implanted in patient 500, to an implanted portion of the processing unit (e.g., processing unit first portion 130*a*) which includes some signal processing elements as well as wireless communication means as has been described in detail in reference to FIG. 2. The implanted multi-conductor cable preferably includes a separate conductor for each electrode, as well as additional conductors to serve other purposes, such as providing reference signals and ground. A processing unit second portion 130*b* receives the wireless communications from the implanted portion. Processing unit second portion 130*b* is removably located just above ear 280 of patient 500, such as to be aligned with an infrared data transmission element of the implanted device. Multicellular signals or derivatives of the multicellular signals are transmitted from the implanted processing unit to processing unit second portion 130*b* for further processing. The processing unit components of system 100 perform various signal processing functions as have been described in detail in reference to FIG. 2. The processing unit may process signals that are mathematically combined, such as combining neuron spikes that are first separated using spike discrimination methods. In alternative embodiments, the processing unit may comprise multiple components or a single component. Each of the processing unit components can be fully implanted in patient 500, be external to the body, or be implanted with a portion of the component exiting through the skin.

In FIG. 3, a first controlled device is a computer including CPU 305 that may be attached to monitor 302 and integrated into configuration cart 121. Through the use of system 100, patient 500 can control one or more computer functions including but not limited to: an on/off function, a reset function, a language function, a modem function, a printer function, an Internet function, a cursor, a keyboard, a joystick, a trackball or other input device. Each function may be controlled individually or in combination. System 100 includes a second controlled device (e.g., wheelchair 310). Numerous other controlled devices can be included in the systems of this application, individually or in combination, including but not limited to: a computer; a computer display; a mouse; a cursor; a joystick; a personal data assistant; a robot or robotic component; a computer controlled device; a teleoperated device; a communication device or system; a vehicle such as a wheelchair; an adjustable bed; an adjustable chair; a remote controlled device; a Functional Electrical Stimulator device or system; a muscle stimulator; an exoskeletal robot brace; an artificial or prosthetic limb; a vision enhancing device; a vision restoring device; a hearing enhancing device; a hearing restoring device; a movement assist device; medical therapeutic equipment such as a drug delivery apparatus; medical diagnostic equipment such as epilepsy monitoring apparatus; other medical equipment such as a bladder control device, a bowel control device and a human enhancement device; closed loop medical equipment and other controllable devices applicable to patients with some form of paralysis or diminished function as well as any device that may be utilized under direct brain or thought control in either a healthy or unhealthy patient.

Processing unit second portion 130*b* includes a unique electronic ID, such as a unique serial number or any alphanumeric or other retrievable, identifiable code associated uniquely with the system 100 of patient 500. The unique electronic identifier may take many different forms in processing unit second portion 130*b*, such as, for example, a piece of electronic data stored in a memory module; a semiconductor element or chip that can be read electronically via serial, parallel or telemetric communication; pins or other conductive parts that can be shorted or otherwise connected to each other or to a controlled impedance, voltage or ground, to create a unique code; pins or other parts that can be masked to create a binary or serial code; combinations of different impedances used to create a serial code that can be read or measured from contacts, features that can be optically scanned and read by patterns and/or colors; mechanical patterns that can be read by mechanical or electrical detection means or by mechanical fit, a radio frequency ID or other frequency spectral codes sensed by radiofrequency or electromagnetic fields, pads and/or other marking features that may be masked to be included or excluded to represent a serial code, or any other digital or analog code that can be retrieved from the discrete component.

Alternatively or in addition to embedding the unique electronic ID in processing unit second portion 130b, the unique electronic ID can be embedded in one or more implanted discrete components. Under certain circumstances, processing unit second portion 130b or another external or implanted component may need to be replaced, temporarily or permanently. Under these circumstances, a system compatibility check between the new component and the remaining system components can be confirmed at the time of the repair or replacement surgery through the use of the embedded unique electronic ID. The unique electronic ID can be embedded in one or more of the discrete components at the time of manufacture, or at a later date such as at the time of any clinical procedure involving the system, such as a surgery to implant the sensor electrodes into the brain of patient 500. Alternatively, the unique electronic ID may be embedded in one or more of the discrete components at an even later date such as during a system configuration routine (e.g., a calibration routine).

Processing unit second portion 130b communicates with one or more discrete components of system 100 via wireless communication means. Processing unit second portion 130b communicates with selector module 400, a component utilized to select the specific device or devices to be controlled by the processed signals of system 100. Selector module 400 includes a touch screen set of buttons, input element 402, used to perform the selection process. Processing unit second portion 130b also communicates with controlled device CPU 305, such as to control a cursor, joystick, keyboard or other function of CPU 305. Processing unit second portion 130b further communicates with processing unit third portion 130c. Processing unit third portion 130c provides additional signal processing functions, as have been described above, to control wheelchair 310. An additional processing unit discrete component (e.g., processing unit fourth portion 130d) may be included to perform additional processing of the multicellular signals and/or derivatives of these processed signals and/or processing of additional data, such as collective processing used to control one or more additional controlled devices of the present invention. System 100 may utilize selector module 400 to select one or more of CPU 305, wheelchair 310, or another controlled device to be controlled by the processed signals produced by the processing unit of the present invention. In system 100 of FIG. 3, one set of processed signals emanate from one portion of the processing unit (e.g., processing unit second portion 130b) and a different set of processed signals emanate from a different portion of the processing unit (e.g., processing unit third portion 130c).

The various components of system 100 communicate with wireless transmission means. However, it should be appreciated that physical cables can be used to transfer data alternatively or in addition to wireless means. These physical cables may include electrical wires, optical fibers, sound wave guide conduits, other physical means of transmitting data, and/or power, and any combination of those means.

A qualified individual, such as an operator 110 in cooperation with patient 500, is performing a patient training routine, one of numerous configuration programs or routines of the system. In an alternative embodiment, patient 500 is the operator of the patient training routine or other configuration routine. The patient training routine may be performed with controlled device 305. Displayed on monitor 302 is planned trajectory 711, system controlled target 712 and patient controlled object 713. In the performance of the patient training routine, multiple time varying stimulus, such as a moving system controlled target 712 are provided to the patient such that the patient can imagine moving that target, and a set of multicellular signals can be collected by the processing unit to produce one or more algorithms to produce the processed signals. In a preferred embodiment, after a first set of multicellular signals is collected, and a first transfer function for producing processed signals is developed, a second set of time varying stimulus is provided in combination with a patient controlled object, such as patient controlled object 713. During the time that the patient tries to mimic the motion of the system controlled target 712 with the visual feedback of the patient controlled target 713, and a second set of multicellular signals is collected and a second, improved transfer function is produced by the system. Additional forms of feedback can be provided to the patient, such as tactile transducer 701 shown attached to patient 500's neck, and speaker 702 shown attached (e.g., fixedly mounted to the back of controlled wheelchair 310) to processing unit third portion 130c. Speaker 702 and tactile transducer 701 can provide feedback in the form of a time varying stimulus, a derivative of the multicellular signals, and/or a representation of the processed signals as controlled by patient 500.

In an embodiment, one or more system configuration routines can be performed without an operator, with the patient as the operator, or with an operator at a remote location such as when the system of the present invention is electronically connected with a computer or computer network such as the Internet. In another embodiment, the patient training routine is performed at least one time during the use of the system, preferably before patient 500 is given, by the system, full control of one or more controlled devices. For example, limited control of CPU 305 may include the ability to send and receive email but not the ability to adjust a computer-controlled thermostat. Limited control of wheelchair 310 may be to turn left or right, but not move forward or back, or to only allow travel at a limited velocity. Limited control may also include no control of one or more controlled devices. Each controlled device will have different parameters limited by system 100 when patient 500 has not been given full control. In an embodiment, the selection of these parameters, the values to be limited, the criteria for achieving full control such as the value of a success threshold achieved during a system configuration routine such as a patient training routine, and any combinations of these may be modified only in a secured way such as only by a clinician utilizing electronic or mechanical keys or passwords.

In addition to successful completion of the patient training routine, completion of one or more other configuration routines may be required for patient 500 to have full control of one or more controlled devices, or multiple successful completions of a single routine. Success is preferably measured through the measurement of one or more performance parameters during or after the configuration routine. Success will be achieved by a performance parameter being above a threshold value, such as a threshold value adjustable only by a clinician, such as a clinician at a remote site utilizing a password, user identification, an electronic ID and/or a mechanical key. These configuration routines are utilized by the system to not only determine the applicability of full control to the patient, but to set or reset one or more system configuration parameters. System configuration parameters include but are not limited to: selection of cellular signals for processing by the processing unit; criteria for the selection of cells for processing; a coefficient of a signal processing function such as amplification, filtering, sorting, conditioning, translating, interpreting, encoding, decoding, combining, extracting, sampling, multiplexing, analog to digital converting, digital to analog converting, mathematically transforming; a control signal transfer function parameter such as a transfer function coefficient, algorithm, methodology, mathematical equation, a calibration parameter such as calibration frequency; a controlled device parameter such as a controlled device boundary limit; acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signal to patient; calibration parameter such as calibration duration and calibration frequency; controlled device parameter such as controlled device mode; alarm or alert threshold; and a success threshold.

As depicted in FIG. 3, operator 110 utilizes configuration apparatus 120 which includes two monitors (first configuration monitor 122a and second configuration monitor 122b), configuration keyboard 123, and configuration CPU 125, to perform a calibration routine or other system configuration process such as a patient training routine, algorithm and algorithm parameter selection and output device setup. The configuration routines, such as the patient training routine, include software programs and hardware required to perform the configuration. The embedded software and/or hardware may be included in the processing unit, such as processing unit second portion 130b, be included in selector module 400, be incorporated into configuration apparatus 120, a controlled device, or combinations of these. Configuration apparatus 120 may include additional input devices, such as a mouse or joystick, or an input device for a patient with limited motion, such as a tongue switch; a tongue palate switch; a chin joystick; a Sip-n-puff joystick controller; an eye tracker device; a head tracker device; an EMG switch such as an eyebrow EMG switch; an EEG activated switch; and a speech recognition device.

Configuration apparatus 120 may include various elements, functions, and data including but not limited to: memory storage for future recall of configuration activities, operator qualification routines, standard human data, standard synthesized or artificial data, neuron spike discrimination software, operator security and access control, controlled device data, wireless communication means, remote (such as via the Internet) configuration communication means and other elements, functions and data used to provide an effective and efficient configuration on a broad base of applicable patients and a broad base of applicable controlled devices. A system electronic ID can be embedded in one or more of the discrete components at the time, including an ID embedded at the time of system configuration. In an alternative embodiment, all or part of the functionality of configuration apparatus 120 is integrated into selector module 400 such that system 100 can perform one or more configuration processes such as a calibration procedure or patient training routine, utilizing selector module 400 without the availability of configuration apparatus 120.

In order to change a system configuration parameter, system 100 includes a permission routine, such as an embedded software routine or software driven interface that allows the operator to view information and enter data into one or more components of system 100. The data entered must signify an approval of the parameter modification in order for the modification to take place. Alternatively, the permission routine may be partially or fully located in a separate device such as configuration apparatus 120 of FIG. 3, or a remote computer such as a computer that accesses system 100 via the Internet or utilizing wireless technologies. In order to access the permission routine, and/or approve the modification of the system configuration parameters, a password or security key, mechanical, electrical, electromechanical or software based, may be required of the operator. Multiple operators may be needed or required to approve a parameter modification. Each specific operator or operator type may be limited by system 100, via passwords and other control configurations, to approve the modification of only a portion of the total set of modifiable parameters of the system. Additionally or alternatively, a specific operator or operator type may be limited to only approve a modification to a parameter within a specific range of values, such as a range of values set by a clinician when the operator is a family member. Operator or operator types, hereinafter operator, include but are not limited to: a clinician, primary care clinician, surgeon, hospital technician, system 100 supplier or manufacturer technician, computer technician, family member, immediate family member, caregiver, and patient.

In a preferred embodiment, the system 100 of FIG. 3 includes an interrogation function, which interrogates the system to retrieve certain data such as on the demand of an operator. Based on the analysis of the data, a recommendation for a parameter value change can be made available to the operator, such as by automatic configuration or calibration routines that are initiated by the operator initiated interrogation function. After viewing the modification, the appropriate operator would approve the change via the permission routine, such as using a computer mouse to click "OK" on a confirmation box displayed on a display monitor, or a more sophisticated, password controlled methodology.

In a preferred embodiment, an automatic or semi-automatic configuration function or routine is embedded in system 100. This embedded configuration routine can be used in place of a configuration routine performed manually by operator 110 as is described hereabove, or can be used in conjunction with one or more manual configurations. Automatic and/or semi-automatic configuration triggering event or causes can take many forms including but not limited to: monitoring of cellular activity, wherein the system automatically changes which particular signals are chosen to produce the processed signals; running parallel algorithms in the background of the one or more algorithms currently used to create the processed signals, and changing one or more algorithms when improved performance is identified in the background event; monitoring of one or more system functions, such as alarm or warning condition events or frequency of events, wherein the automated system shuts down one or more functions and/or improves performance by changing a relevant variable; and other methods that monitor one or more pieces of system data, identify an issue or potential improvement, and determine new parameters that would reduce the issue or achieve an improvement.

In an exemplary embodiment, when specific system configuration parameters are identified, by an automated or semi-automated calibration or other configuration routine, to be modified for the reasons described above, an integral permission routine of the system requires approval of a specific operator when one or more of the system configuration parameters are modified.

Operator 110 may be a clinician, technician, caregiver, patient family member or even the patient themselves in some circumstances. Multiple operators may be needed or required to perform a configuration routine or approve a modification of a system configuration parameter, and each operator may be limited by system 100, via passwords and other control configurations, to only perform or access specific functions. For example, only the clinician may be able to change specific critical parameters, or set upper and lower limits on other parameters, while a caregiver, or the patient, may not be able to access those portions of the configuration procedure or the permission procedure. The configuration routine includes the setting of numerous parameters needed by system 100 to properly control one or more controlled devices. The parameters include but are not limited to various signal conditioning parameters as well as selection and de-selection of specific multicellular signals for processing to generate the device control creating a subset of signals received from the sensor to be processed. The various signal conditioning parameters include, but are not limited to: threshold levels for amplitude sorting, other sorting and pattern recognition parameters, amplification parameters, filter parameters, signal conditioning parameters, signal translating parameters, signal interpreting parameters, signal encoding and decoding parameters, signal combining parameters, signal extracting parameters, mathematical parameters including transformation coefficients and other signal processing parameters used to generate a control signal for transmission to a controlled device.

The configuration routine will result in the setting of various system configuration output parameters, all such parameters to be considered system configuration parameters. Configuration output parameters may include but be not limited to: electrode selection, cellular signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In a preferred embodiment, the configuration output parameters are stored in memory in one or more discrete components, and the parameters are linked to the system's unique electronic ID.

Calibration, patient training, and other configuration routines, including manual, automatic and semi-automatic routines, may be performed on a periodic basis, and may include the selection and deselection of specific cellular signals over time. The initial configuration routine may include initial values, or starting points, for one or more of the configuration output parameters. Setting initial values of specific parameters, may invoke a permission routine. Subsequent configuration routines may involve utilizing previous configuration output parameters that have been stored in a memory storage element of system 100. Subsequent configuration routines may be shorter in duration than an initial configuration and may require less patient involvement. Subsequent configuration routine results may be compared to previous configuration results, and system 100 may require a repeat of configuration if certain comparative performance is not achieved.

The configuration routine may include: (a) setting a preliminary set of configuration output parameters; (b) generating processed signals to control the controlled device; (c) measuring the performance of the controlled device control; and (d) modifying the configuration output parameters. The configuration routine may further include the steps of repeating steps (b) through (d). The configuration routine may also require invoking a permission routine.

In the performance of a configuration routine, the operator 110 may involve patient 500 or perform steps that do not involve the patient. In the patient training routine and other routines, the operator 110 may have patient 500 imagine one or more particular movements, imagined states, or other imagined events, such as a memory, an emotion, the thought of being hot or cold, or other imagined event not necessarily associated with movement. The patient participation may include: the patient training routine providing one or more time varying stimulus, such as audio cues, visual cues, olfactory cues, tactile cues, moving objects on a display such as a computer screen, moving mechanical devices such as a robotic arm or a prosthetic limb, moving a part of the patient's body such as with an exoskeleton or FES implant, changing audio signals, changing electrical stimulation such as cortical stimulation, moving a vehicle such as a wheelchair or car; moving a model of a vehicle; moving a transportation device; and other sensory stimulus. The imagined movements may include the imagined movement of a part of the body, such as a limb, arm, wrist, finger, shoulder, neck, leg, angle, and toe, as well as imagining moving to a location, moving in a direction, moving at a velocity or moving at an acceleration.

The patient imagines moving system controlled target 712 along planned trajectory 711, as target 712 is moving as controlled by the system or manually by operator 110. The current processed signal, hereinafter a representation of the processed signal, available by applying a transfer function to the multicellular signals detected during the imagined movement or other step of the patient training routine, is displayed in the form of control of patient controlled target 713. The transfer function is preferably based on multicellular signals stored during a previous imagined movement, or multiple previous imagined movements, preferably two or more sets of states of time varying stimulus. The representation of the processed signal may mimic the time varying stimulus, similar to patient controlled object 713 being a similar form to system controlled object 712.

Alternatively, the time varying stimulus and representation of the processed signals may take different forms, such as a time varying stimulus including an object on a visual display, wherein the representation is a moving mechanical structure, or the stimulus being a moving mechanical structure and the representation comprising an object on a visual display. The representation of the processed signals can be provided to the patient in visual form such as a visual representation of limb motion displayed on a computer monitor, or in one or more sensory forms such as auditory, olfactory, gustatory, and electrical stimulation such as cortical stimulation. The representation of the processed signals can be provided in combinations of these and other forms.

In some exemplary embodiments, the first patient training step may not include patient controlled object 713, or it may include a patient controlled target whose processed signal is not based on a set of multicellular signals collected during a previous imagined movement. Multiple steps of providing a set of states of the time varying stimulus and recording the multicellular signal data may involve different subsets of cells from which the multicellular signals are detected. Also, different sets of states of time varying stimulus may have different numbers of cells in each. Alternative to the system controlled target 712 along planned trajectory 711, the patient may imagine movements while viewing a time varying stimulus comprising a video or animation of a person performing the specific movement pattern. In a preferred embodiment, this visual feedback is shown from the patient's perspective, such as a video taken from the person performing the motion's own eye level and directional view. Multiple motion patterns and multiple corresponding videos may be available to improve or otherwise enhance the patient training process. The patient training routine temporally correlates a set of states of the time varying stimulus with the set of multicellular signal signals captured and stored during that time period, such that a transfer function can be developed for future training or controlled device control. Correlations can be based on numerous variables of the motion including but not limited to: position, velocity and acceleration of the time varying stimulus; a patient physiologic parameter such as heart rate; a controlled device parameter; a system environment parameter; a password controlled parameter; a clinician controlled parameter; and a patient training routine parameter. In the patient training routine of FIG. 3, the controlled device, CPU 305 and controlled monitor 302 are used in the patient training routine to display the time varying stimulus as well as the representation of the processed signal. In a subsequent step, wheelchair 310 can also be employed, such as by a system controlling the wheelchair while the patient imagines the control, the wheelchair movement being the time varying stimulus.

During the time period that a set of states of the time varying stimulus is applied, multicellular signal data detected by the implanted sensor is stored and temporally correlated to that set of states of the time varying stimulus provided to the patient. In a preferred embodiment, the system of the present invention includes a second patient training routine and a second controlled device, wherein the first patient training routine is used to configure the first controlled device and the second patient training routine is used to configure the second controlled device. The two patient training routines may include different time varying stimulus, chosen to optimize the routine for the specific controlled device, such as a moving cursor for a computer mouse control system, and a computer simulated prosthetic limb for a prosthetic limb control system. In a preferred system, the first controlled device is a prosthetic arm and the second controlled device is a prosthetic leg, this system having two different time varying stimulus in the two corresponding patient training routines.

In one embodiment, the first controlled device is a prosthetic arm and the second controlled device is a wheelchair. This system may also have two different time varying stimulus in the two corresponding patient training routines. In an alternative, preferred embodiment, a controlled device surrogate is utilized in the patient training routine. The controlled device surrogate preferably has a larger value of one or more of: degrees of freedom; resolution; modes; discrete states; functions; and boundary conditions. Numerous boundary conditions with greater values for the surrogate device can be employed. Such boundary conditions may include: maximum distance; maximum velocity; maximum acceleration; maximum force; maximum torque; rotation; and position. The surrogate device employing larger values of these parameters creates the scenario, wherein the patient is trained and/or tested with a device of more complexity than the eventual controlled device to be used.

The time varying stimulus may be supplied to the patient in numerous forms such as visual, tactile, olfactory, gustatory, and electrical stimulation such as cortical stimulation. The time varying stimulus may be moved around manually, automatically produced and controlled by a component of the system such as the processing unit, or produced by a separate device. The time varying stimulus may include continuous or semi-continuous motion of an object, such as an object moving on a visual display, a mechanical object moving in space, or a part of the patient's body moving in space. The time varying stimulus may be of a short duration, such as an object appearing and disappearing quickly on a display, or a flash of light.

In an embodiment, the patient training routine includes multiple forms of feedback, in addition to the time varying stimulus, such feedback provided to the patient in one or more forms including but not limited to: visual; tactile; auditory; olfactory; gustatory; and electrical stimulation. The additional feedback may be a derivative of the multicellular signals, such as visual or audio feedback of one or more neuron spike modulation rates. Different forms of feedback may be provided as based on a particular device to be controlled by the processed signals. Numerous parameters for the time varying stimulus and other feedback may be adjustable, such as by an operator such as the patient. These parameters including but not limited to: sound volume and frequency; display brightness, contrast, size and resolution; display object size; electrical current parameter such as current or voltage; mechanical or visual object size, color, configuration, velocity or acceleration; and any combinations of these.

A configuration routine such as a calibration or patient training routine may utilize one or more configuration input parameters to determine one or more system output parameters used to develop a processed signal transfer function. In addition to the multicellular signals themselves, system or controlled device performance criteria can be utilized. Other configuration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including but not limited to modulation of any signal property. Additional configuration input parameters include but are not limited to: system performance criteria, controlled device electrical time constants, controlled device mechanical time constants, other controlled device criteria, types of electrodes, number of electrodes, patient activity during configuration, target number of signals required, patient disease state, patient condition, patient age and other patient parameters and event based (such as a patient imagined movement event) variations in signal properties including neuron firing rate activity. In a preferred embodiment, one or more configuration input parameters are stored in memory and linked to the embedded, specific, unique electronic identifier. All configuration input parameters shall be considered a system configuration parameter of the system.

In some exemplary embodiments, it may be desirous for the configuration routine to exclude one or more multicellular signals based on a desire to avoid signals that respond to certain patient active functions, such as non-paralyzed functions, or even certain imagined states. The configuration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor. In a preferred embodiment, an automated or semi-automated calibration or other configuration routine may include through addition, or exclude through deletion, a signal based on insufficient activity during known patient movements.

The configuration routines of the system of the present invention, such as a patient training routine in which a time varying stimulus is provided to the patient, may conduct adaptive processing, such as adapting between uses or within a single patient training routine. The adaptation may be caused by a superior or inadequate level of performance, as compared to a threshold value, such as an adjustable threshold value. In a preferred embodiment, performance during a patient training routine above a threshold value causes the duration of the routine to decrease, and performance below a threshold value causes the duration of the routine to increase. Control of the controlled device or surrogate controlled device is a preferred way of measuring performance. Alternatively, a change in multicellular signals, such as a change in modulation rate may cause an adaptation to occur. A monitored difference is a first patient training event and a second patient training event, such as a difference in signal modulation, may cause an adaptation in the patient training routine, such as to preferentially choose one time varying stimulus over another time varying stimulus. Other causes include a change to a patient parameter, such as the level of patience consciousness. In a preferred embodiment, at a low level of consciousness, the patient training routine changes or discontinues. The level of consciousness may be determined by the multicellular signals detected by the sensor. Alternatively, the level of consciousness can be detected utilizing a separate sensor, such as a sensor to detect EEG or LFP signals. The patient training routine may automatically adapt, such as due to a calculation performed by the processing unit, or may adapt due to operator input.

In an exemplary embodiment, the system may include a processing unit that processes multicellular signals received from patient 500. Processing unit second portion 130b and other processing unit components, singly or in combination, perform one or more functions. The functions performed by the processing unit include but are not limited to: producing the processed signals; transferring data to a separate device; receiving data from a separate device; producing processed signals for a second controlled device; activating an alarm, alert or warning; shutting down a part of or the entire system; ceasing control of a controlled device; storing data; and performing a configuration.

In order for the processing unit of system 100 to perform one or more functions, one or more system configuration parameters are utilized. These parameters include pieces of data stored in, sent to, or received from, any component of system 100, including but not limited to: the sensor; a processing unit component; processing unit second portion 130b; or a controlled device. Parameters can be received from devices outside of system 100 as well, such as configuration apparatus 120, a separate medical therapeutic or diagnostic device, a separate Internet based device, or a separate wireless device. These parameters can be numeric or alphanumeric data, and can change over time, either automatically or through an operator involved configuration or other procedure.

The processing unit, or other component of system 100 may produce multiple processed signals for controlling one or more controlled device. This second processed signal may be based on multicellular signals of the sensor, such as the same set of cells as the first processed signal is based on, or a different set of cells emanating signals. The signal processing used to produce the additional processed signals can be the same as the first, or utilize different processing, such as different transfer functions. Transfer functions may include different algorithms, coefficients such as scaling factors, different types of feedback, and other transfer function variations. Alternatively, the additional processed signals may be based on signals not received from the sensor in which the first processed signal is derived. An additional sensor, such as a similar or dissimilar sensor, may provide the signals to produce the additional processed signals, or the system may receive a signal from an included input device such as a tongue switch; tongue palate switch; chin joystick; Sip-n-puff joystick controller; eye gaze tracker; head tracker; EMG switch such as eyebrow EMG switch; EEG activated switch; speech recognition device; and any combinations thereof. The additional processed signal may be derived from a monitored biological signal such as a signal based on eye motion; eyelid motion; facial muscle activation or other electromyographic activity; heart rate; EEG; LFP; respiration; and any combinations thereof. In creating the additional processed signal or signals, the processing unit may convert these alternative input signals into a digital signal, such as a digital signal used to change the state of the system, such as a change in state of an integrated configuration routine.

Figure 4:
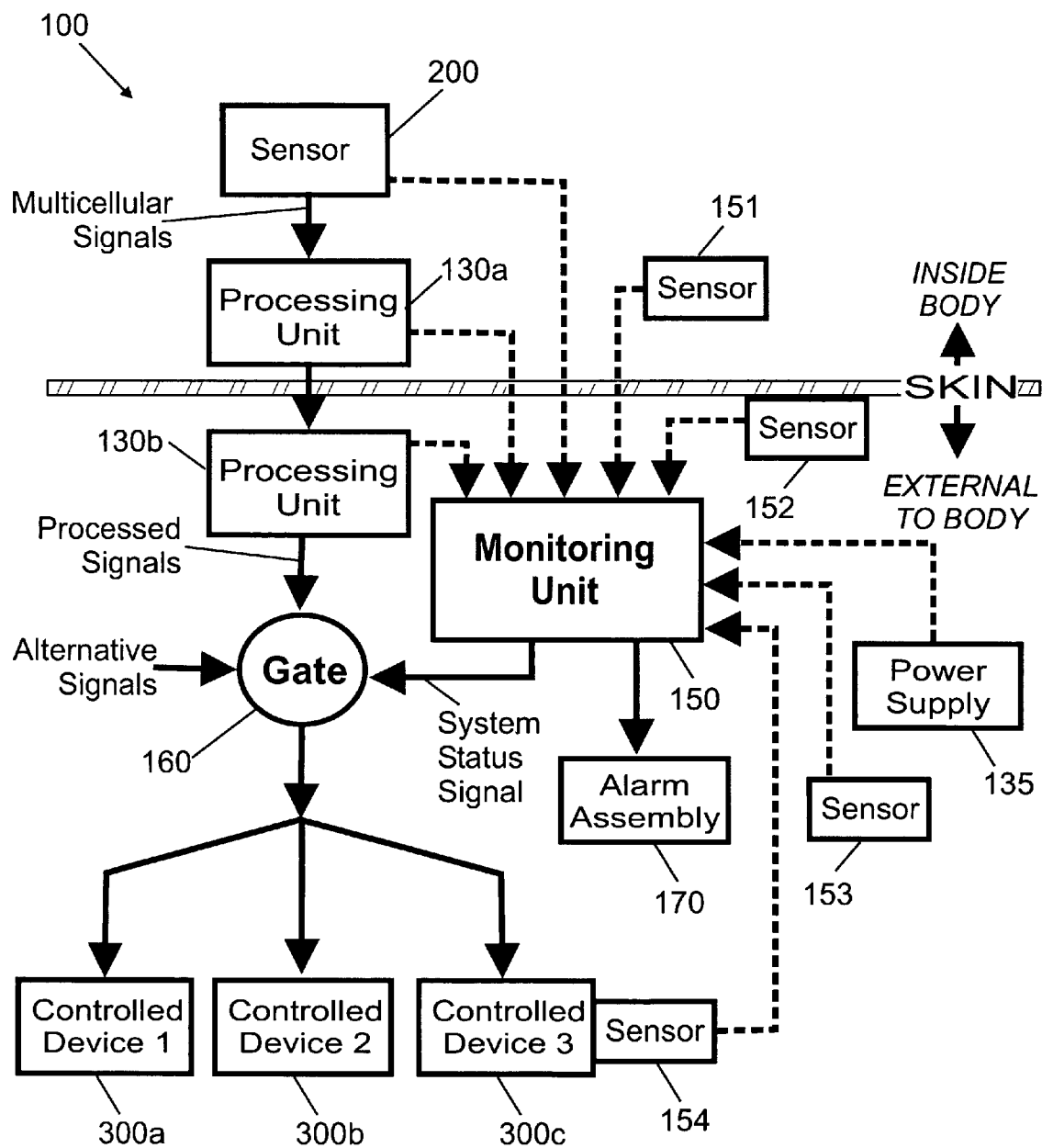
FIG. 4 illustrates a schematic representation of another exemplary embodiment of a biological interface system, consistent with the present invention, wherein multiple controlled devices and multiple sensors are integral to the system.

Referring now to FIG. 4, another exemplary embodiment of the biological interface system is illustrated, in which the monitoring unit receives multiple feedback signals containing system data, and the signal gate transmits signals to multiple controlled devices. System 100, schematically depicted as showing implanted and external system components, includes monitoring unit 150 which receives multiple feedback signals (depicted in FIG. 4 as dotted lines) from multiple discrete components of system 100. Monitoring unit 150 produces a system status signal that signal gate 160 uses to select the processed signal received from processing unit second portion 140b or the alternative signal generated by the system to be sent to one or more controlled devices. System 100 further includes sensor 200, preferably a multi-electrode sensor implanted in the brain of the patient, which is electrically connected to another implant, such as processing unit first portion 130a. Processing unit first portion 130a transmits signal across the skin and other tissue to processing unit second portion 130b, such as via infrared or wireless communications. Processing unit first portion 130a and processing unit second portion 130b comprise the processing unit of the present invention, using various signal processing techniques to produce processed signals to control a device.

System 100, further comprises an implanted sensor 151, such as a blood glucose sensor or other physiologic sensor, which, in addition to sensor 200 and processing unit 130a, transmits signals to monitoring unit 150 for generation of the system status signal. A skin-attached sensor 152 is included, such as an EKG sensor, such that when an unacceptable heart rate is detected, an unacceptable condition is determined by monitoring unit 150. Both implanted sensor 151 and sensor 152 can be used to alternatively or additionally provide data for patient parameters selected from the group consisting of: EKG; respiration; blood glucose; temperature; blood pressure; EEG; perspiration; and any combination thereof. Sensor 153 is an environmental sensor, such as a temperature sensor or an electromagnetic field sensor. Monitoring unit 150 can determine an unacceptable temperature or an unacceptable electromagnetic field detected, such as an unacceptable electromagnetic field strength and/or frequency range. Each of these pieces of system data can be compared to one or more thresholds to identify an unacceptable condition that triggers the system status signal generated by monitoring unit 150 to cause signal gate 160 to transmit the alternative signal instead of the processed signal to one or more controlled devices.

System 100, further comprises power supply 135, such as a rechargeable battery, and data about the power level is transmitted to monitoring unit 150 such that a power level below a threshold value indicates an unacceptable condition. Power supply 135 may provide power to one or more external components of system 100. In a preferred embodiment, processing unit second portion 130b inductively transmits power from an integral coil to an integral coil of processing unit first portion 130a, such that power supply 135 indirectly supplies power to one or more implanted components as well as one or more external components. System 100 further includes multiple controlled devices (e.g., first controlled device 300a, second controlled device 300b, and third controlled device 300c). Each controlled device can be one of the many types and forms described with reference to FIG. 2 and FIG. 3 hereabove. In an embodiment, the three controlled devices are three prosthetic limbs or three exoskeleton devices. In an alternate embodiment, the three controlled devices comprise an FES device, a wheelchair, and a computer. Many different configurations of multiple devices that can be controlled by electronic and other signals are applicable and should be considered to be within the scope of this application. Each controlled device can produce system data to be transmitted to monitoring unit 150, such as sensor 154, that is integral to third controlled device 300c and preferably comprises a force transducer used to prevent an unacceptable force generated by controlled device 300c. Other controlled device parameters can be monitored by sensor 154 or other suitable means such as to provide system data in the form of: controlled device orientation; controlled device contact with a surface; controlled device position measurement; controlled device force measurement; controlled device power measurement; controlled device environment measurement; and any combinations thereof. Controlled device data can also include the status of a failure or undesired value of a parameter achieved.

In some exemplary embodiments, the system may be configured to perform a routine for creating two or more time codes of cellular data, such as a temporally correlated map of neural spike activity. The processing unit uses one of these maps to produce the processed signals, and the other, which may be too complex to operate in real time, can simply log the spike activity in memory. The monitoring unit 150 compares the two maps of neural spike activity, and when the comparison yields a measure of difference in the two maps that is at or above a threshold value, such as a statistical difference in populations, an unacceptable condition is identified. System 100 may include various diagnostic routines that run continuously or on a discrete basis, wherein the output of the diagnostic routine is system data that is processed by monitoring unit 150 to generate the system status signal. Additional sensors, such as those of FIG. 4, can be used by these system diagnostic routines to generate the system data of the present invention. In a preferred embodiment, system 100 includes one or more detachable cables, and a sensor can be used to confirm proper attachment of that cable. When inadequate attachment is detected at an improper time, monitoring unit 150 generates a system control signal to cause signal gate 160 to transmit the alternate signal to the appropriate controlled device. In another embodiment, system 100 includes a patient input device, such as has been described in detail hereabove. A sensor may be included in the input device, the sensor producing system data representative of a parameter of the input device, such as a parameter indicating adequate functionality. This sensor data is received by the processing unit and analyzed to produce the system status signal.

In the embodiment of FIG. 4, the system status signal generated by monitoring unit 150 has three or more states. These different states correspond to two or more different alternate signals, or two or more controlled devices that receive or don't receive the processed signals or the different alternate signals. These multiple states may correspond to conditions that are applicable to a specific controlled device, or specific to a level of an unacceptable condition. One state may allow processed signals to be transmitted to a controlled computer, but not a controlled wheelchair. Another state may allow an exoskeleton to move certain joints, but not others. The system 100 of FIG. 4 embodies a matrix of states for the system status signal, an array of alternate signals, and an array of controlled devices, that can be configured such that signal gate 160 connects certain signals to certain controlled devices based on a pre-determined correlation of the matrices.

In another embodiment, system 100 may be attached to a computer network such as the Internet. One or more components, such as processing unit second portion 130b and/or monitoring unit 150, can send and receive data via wired or wireless means, to a remote location's computer. This connection allows remote access of an operator to perform a system configuration or other routine. The connection also allows system 100 to access information at a remote site. With the connection to remote computers and other network devices, the potential of exposure to a computer virus is increased. In an embodiment, system 100 includes a virus detection routine. When a virus has been detected, in addition to one or more other safeguarding actions, monitoring unit 150 transmits a system status signal to cause the gate 160 to transmit the alternate signal instead of the processed signal to the controlled device 300. The virus routine can periodically be updated via the computer network to contain the best available information and detection schemes regarding computer viruses and other system checking information.

System 100 of FIG. 4 further includes an alarm assembly 170. Alarm assembly 170 receives a signal from monitoring unit 150 that is used by alarm assembly 170 to trigger one or more events. In an embodiment, alarm assembly 170 alerts the patient when the alternate signal is being sent to one or more controlled devices, such as via an audible transducer or visual message (e.g., a message displayed on one or more screens integral to system 100). Alarm assembly 170 may include a telephone and dialing functionality such that a person remote from the patient can be notified of the unacceptable condition detected by monitoring unit 150. Alarm assembly 170 may be activated by one or more states of the system status signal, or by another signal or state generated by monitoring unit 150. In another embodiment, a reset routine of the system, such as a routine requiring a long depression of an integral switch, may be used to deactivate alarm assembly 170 after it has been activated.

Numerous methods are provided in the multiple embodiments of the disclosed invention. An exemplary embodiment includes a method of gating a control signal to a controlled device. The method comprises: providing a biological interface system for collecting multicellular signals emanating from one or more living cells of a patient and for transmitting processed signals to control a device. The biological interface system comprises: a sensor comprising a plurality of electrodes for detecting the multicellular signals; a processing unit for receiving the multicellular signals from the sensor for processing the multicellular signals to produce processed signals and for transmitting the processed signals; a monitoring unit for receiving system data and for processing the system data to produce a system status signal; an alternate signal generated by the system; and a signal gate for receiving the processed signal from the processing unit, for receiving the alternative signal generated by the system, for receiving the system status signal from the monitoring unit, and for transmitting the control signal to the controlled device. The monitoring unit, based on the analysis of the system data, transmits a system status signal that determines whether the control signal, sent by the signal gate, comprises the processed signal or the alternative signal.

It should be understood that numerous other configurations of the systems, devices, and methods described herein could be employed without departing from the spirit or scope of this application. For example, the system may include multiple functional components, such as a sensor for detecting multicellular signals, a processing unit for processing the multicellular signals to produce processed signals, and the controlled device that is controlled by the processed signals. Different from the logical components are physical or discrete components, which may include a portion of a logical component, an entire logical component and combinations of portions of logical components and entire logical components. These discrete components may communicate or transfer data to or from each other, or communicate with devices outside the system. In each system, physical wires, such as electrical wires or optical fibers, can be used to transfer data between discrete components, or wireless communication means can be utilized. Each physical cable can be permanently attached to a discrete component or can include attachment means to allow attachment and potentially allow, but not necessarily permit, detachment. Physical cables can be permanently attached at one end and include attachment means at the other.

The sensors of the systems of this application can take various forms, including multiple discrete component forms, such as multiple penetrating arrays that can be placed at different locations within the body of a patient. The processing unit of the systems of this application can also be contained in a single discrete component or multiple discrete components, such as a system with one portion of the processing unit implanted in the patient, and a separate portion of the processing unit external to the body of the patient. The sensors and other system components may be utilized for short term applications, such as applications less than twenty four hours, sub-chronic applications such as applications less than thirty days, and chronic applications. Processing units may include various signal conditioning elements such as amplifiers, filters, signal multiplexing circuitry, signal transformation circuitry and numerous other signal processing elements. In some embodiments, an integrated spike sorting function may be included. The processing units performs various signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controllable device. The processing unit utilizes numerous algorithms, mathematical methods, and software techniques to create the desired control signal. The processing unit may utilize neural net software routines to map cellular signals into desired device control signals. Individual cellular signals may be assigned to a specific use in the system. The specific use may be determined by having the patient attempt an imagined movement or other imagined state. For most applications, it is preferred that that the cellular signals be under the voluntary control of the patient. The processing unit may mathematically combine various cellular signals to create a processed signal for device control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A biological interface system comprising:
   a sensor comprising a plurality of electrodes for detecting multicellular signals emanating from one or more living cells of a patient;
   a processing unit configured to receive the multicellular signals from the sensor and process the multicellular signals to produce a processed signal; and
   a signal gate configured to receive the processed signal from the processing unit and an alternative signal generated by the system, the signal gate being configured to transmit a control signal to a controlled device based on either the processed signal or the alternative signal,
   wherein a monitoring unit receives system data and processes the system data to produce a system status signal, and wherein the system status signal determines which of the processed signal and the alternative signal is to be used as the control signal.

2. The system of claim 1, wherein the monitoring unit is configured to compare the system data to a predetermined threshold value.

3. The system of claim 2, wherein the threshold value is adjustable.

4. The system of claim 3, wherein the system is configured to perform an integral permission routine for approving an operator to adjust the threshold prior to an adjustment of the threshold value.

5. The system of claim 3, wherein the system is configured to allow an adjustment of the threshold vale to be performed at a location remote from the patient.

6. The system of claim 5, the system is configured to allow the adjustment of the threshold value to be performed via the Internet.

7. The system of claim 1, wherein the monitoring unit includes an integral safety level parameter used by a mathematical algorithm of the monitoring unit to produce the system status signal.

8. The system of claim 7, wherein the integral safety level parameter is adjustable.

9. The system of claim 8, wherein the system is configured to allow an adjustment of the integral safety level parameter to be performed at a location remote from the patient.

10. The system of claim 9, wherein the system is configured to allow the adjustment to be performed via the Internet.

11. The system of claim 1, wherein the system data comprises multiple system configuration parameters.

12. The system of claim 11, wherein the monitoring unit is configured to perform a correlation assessment of two or more system configuration parameters, wherein the control signal uses the alternative signal when an unacceptable correlation is confirmed.

13. The system of claim 12, wherein the multiple system configuration parameters comprise a first system configuration parameter and a second system configuration parameter, wherein the first system configuration parameter comprises the status of the processed signal, and the second system configuration parameter comprises the status of the control signal.

14. The system of claim 1, wherein the multicellular signals comprise neural signals.

15. The system of claim 1, further comprising a drug delivery system, wherein the processing unit transmits a signal to the drug delivery system to deliver a therapeutic agent to at least a portion of the patient's body.

16. The system of claim 15, wherein the two or more electrical conduits transmit the multicellular signals between at least a portion of the sensor and at least a portion of the processing unit.

17. The system of claim 15, wherein the monitoring unit processing includes an assessment of the magnitude of cross-talk between the two or more conduits, wherein the control signal comprises the alternative signal when the cross-talk magnitude is at or above a threshold value.

18. The system of claim 15, wherein the monitoring unit is configured to assess an impedance of one or more of the electrical conduits, and wherein the control signal uses the alternative signal when impedance is above or below a threshold value.

19. The system of claim 1, further comprising two or more electrical conduits for transmitting the multicellular signals, wherein the system data includes at least a portion of the multicellular signals.

20. The system of claim 1, wherein the system data comprises data relating to the processed signal produced by the processing unit.

21. The system of claim 20, wherein the monitoring unit is configured to assess the noise level of at least part of the processed signal, and wherein the control signal uses the alternative signal when the noise level is at or above a threshold value.

22. The system of claim 20, wherein the processed signal controls a parameter of the controlled device selected from the group consisting of: position; velocity; acceleration; torque; force; and any combination thereof.

23. The system of claim 1, wherein the system data comprises data regarding a communication error in a communication between one or more components of the system, and wherein the control signal uses the alternative signal when the communication error is at or above a threshold value.

24. The system of claim 23, wherein the threshold value comprises a type of communication error.

25. The system of claim 23, wherein the threshold value comprises a quantity of communication error.

26. The system of claim 1, further comprising a second sensor for producing at least a portion of the system data.

27. The system of claim 26, wherein the second sensor is configured to produce data relating to the environment proximate the patient.

28. The system of claim 27, wherein the environment data comprises temperature data.

29. The system of claim 27, wherein the environment data comprises electromagnetic field data.

30. The system of claim 29, wherein the control signal uses the alternative signal when the electromagnetic field is at or above a threshold value.

31. The system of claim 26, wherein the second sensor is affixed to a skin of the patient.

32. The system of claim 26, wherein the second sensor is implanted within the patient.

33. The system of claim 26, wherein the second sensor is configured to produce data relating to the patient's physiologic parameter.

34. The system of claim 33, wherein the patient parameter comprises one or more of: EKG; respiration; blood glucose; temperature; blood pressure; EEG; perspiration; and any combination thereof.

35. The system of claim 1, wherein the system data comprises data relating to the controlled device.

36. The system of claim 35, wherein the controlled device comprises a second sensor for producing the data relating to the controlled device.

37. The system of claim 36, wherein the data produced by the second sensor comprises at least one of: controlled device orientation; controlled device contact with a surface; controlled device position measurement; controlled device force measurement; controlled device power measurement; controlled device environment measurement; and any combination thereof.

38. The system of claim 35, wherein the data relating to the controlled device comprises one or more of: controlled device failure data; controlled device performance data; and controlled device parameter data.

39. The system of claim 1, further comprising a power supply.

40. The system of claim 39, wherein the system data comprises power level data.

41. The system of claim 1, wherein the system is configured to create a time code of specific cellular activity.

42. The system of claim 41, wherein the time code represents neural spike activity.

43. The system of claim 41, wherein an embedded software routine is used in creating the time code.

44. The system of claim 41, wherein creating the time code is an automated routine.

45. The system of claim 41, wherein the system is configured to create a time code of specific neural activity, and wherein the monitoring unit is configured to compare the time code of specific cellular activity and the time code of specific neural activity.

46. The system of claim 45, wherein the control signal uses the alternative signal when a comparison indicates a difference in the time codes that is at or above a threshold value.

47. The system of claim 1, wherein the system is configured to check for a computer virus.

48. The system of claim 47, wherein the system data comprises virus status data.

49. The system of claim 48, wherein the control signal uses the alternative signal when the virus status data is indicative of a virus infection.

50. The system of claim 48, further comprising a connection to a computer network or the Internet.

51. The system of claim 50, wherein the system is configured to update the virus status data via the computer network or the Internet.

52. The system of claim 1, further comprising a detachable cable and a sensor that produces data indicative of proper attachment of the detachable cable.

53. The system of claim 52, wherein the system data comprises the proper attachment data.

54. The system of claim 52, wherein the control signal uses the alternative signal when the attachment data is indicative of the detachable cable not being properly attached.

55. The system of claim 1, further comprising a patient input device.

56. The system of claim 55, wherein the patient input device is selected from the group consisting of: chin joystick; eyebrow EMG switch; EEG activated switch; eye tracker; a head tracker; neck movement switch; shoulder movement switch; sip-n-puff joystick controller; speech recognition switch; tongue switch; and any combination thereof.

57. The system of claim 55, wherein the system data includes data indicative of a status of the input device.

58. The system of claim 57, wherein the control signal uses the alternative signal when the status of the input device is at an unacceptable state.

59. The system of claim 1, wherein the system status signal comprises three or more states.

60. The system of claim 59, wherein the system is configured to generate a second alternative signal.

61. The system of claim 60, wherein the control signal uses the processed signal when the system status signal is at a first state; the control signal uses the alternative signal when the system status signal is at a second state; and the control signal uses the second alternative signal when the system status signal is at a third state.

62. The system of claim 1, wherein the system is configured to generate a second alternative signal.

63. The system of claim 1, wherein the alternative signal comprises a null signal.

64. The system of claim 1, wherein the alternative signal comprises a derivative of the processed signal.

65. The system of claim 1, wherein the alternative signal causes the controlled device to enter into a safe mode.

66. The system of claim 65, wherein the controlled device comprises a prosthetic limb, and the safe mode includes the prosthetic limb moving to a position to protect at least a portion of the patient's body.

67. The system of claim 66, wherein the portion of the patient's body comprises the patient's head.

68. The system of claim 1, further comprising a second controlled device.

69. The system of claim 1, further comprising an embedded ID.

70. The system of claim 69, wherein the embedded ID is configured to check compatibility of one or more discrete components of the system.

71. The system of claim 70, wherein the signal gate further transmits the control signal to the second controlled device.

72. The system of claim 70, wherein a second control signal is transmitted to the second controlled device by the gate.

73. The system of claim 72, wherein the control signal uses the processed signal, and the second control signal uses the alternative signal.

74. The system of claim 1, further comprising a second gate and a second controlled device, wherein the second gate transmits a second control signal to the second controlled device.

75. The system of claim 74, wherein the second control signal uses the processed signal or the alternative signal.

76. The system of claim 74, wherein the system is configured to generate a second alternative signal, wherein the second control signal uses the processed signal or the second alternative signal.

77. The system of claim 1, wherein the signal gate latches when the gate transitions from transmitting the processed signal to transmitting the alternate signal, such that the gate continues to transmit the alternate signal subsequent to a condition that initially caused the alternate signal to be transmitted is reversed.

78. The system of claim 77, wherein the signal gate remains latched until a reset of the system or a portion of the system is performed.

79. The system of claim 1, wherein the signal gate transmits the processed signal to the controlled device when the system data is in a first state as determined by the monitoring unit; wherein the signal gate subsequently transmits the alternate signal to the controlled device when the system data is in a second state as determined by the monitoring unit; and wherein the signal gate again transmits the processed signal to the controlled device when the system data is subsequently again in the first state as determined by the monitoring unit.

80. The system of claim 1, wherein the signal gate transmits the processed signal to the controlled device when the system data is in a first state as determined by the monitoring unit; wherein the signal gate transmits the alternate signal to the controlled device when the system data is subsequently in a second state as determined by the monitoring unit; and wherein the signal gate maintains transmitting the alternate signal to the controlled device when the system data is subsequently in a third state as determined by the monitoring unit.

81. The system of claim 80, wherein the third state is equivalent to the first state.

82. The system of claim 81, wherein the signal gate transmits the processed signal when the system data is in the third state and a reset of the system or a portion of the system is performed.

83. The system of claim 80, wherein the signal gate transmits the processed signal when the system data is in the third state and a reset of the system or a portion of the system is performed.

84. The system of claim 83, wherein the system is configured to perform a system diagnosis and confirm a system acceptability.

85. The system of claim 1, further comprising an alarm assembly.

86. The system of claim 85, wherein the alarm assembly comprises an audible transducer.

87. The system of claim 85, wherein the alarm assembly comprises a dialing device to dial a predetermined phone number and transmit a predetermined message.

88. The system of claim 85, wherein the alarm assembly is activated when the control signal uses the alternative signal.

89. The system of claim 1, wherein the system is configured to reset at least portion of the system.

90. The system of claim 89, wherein the reset is activated from a remote location.

91. The system of claim 89, wherein the reset is activated by the patient.

92. The system of claim 89, wherein activation of the reset invokes a system permission routine.

93. The system of claim 1, wherein the system comprises a neural interface system.

94. The system of claim 1, wherein the system is configured to provide a therapeutic benefit.

95. The system of claim 94, wherein the therapeutic benefit comprises treatment of one or more of: obesity; an eating disorder; a neurological disorder; a stroke; a coma; amnesia; irregular blood flow in the brain; a psychiatric disorder; depression; a cardiovascular disorder; an endocrine disorder; sexual dysfunction; incontinence; a hearing disorder; a visual disorder; a sleeping disorder; a movement disorder; impaired limb function; absence of a limb or a limb portion; a speech disorder; a physical injury; migraine headaches; chronic pain and other severe pain conditions; and any combination thereof.

96. The system of claim 1, wherein the system is configured to perform a patient diagnosis.

97. The system of claim 96, wherein the patient diagnosis comprises one or more of: obesity; an eating disorder; a neurological disorder; a stroke; a coma; amnesia; irregular blood flow in the brain; a psychiatric disorder; depression; a cardiovascular disorder; an endocrine disorder; sexual dysfunction; incontinence; a hearing disorder; a visual disorder; a sleeping disorder; a movement disorder; impaired limb function; absence of a limb or a limb portion; a speech disorder; a physical injury; migraine headaches; chronic pain and other severe pain conditions; and any combination thereof.

98. The system of claim 1, wherein the system is configured to restore a patient function.

99. The system of claim 98, wherein the patient function comprises one or more of: vision; hearing; speech; communication; limb motion; ambulation; reaching; grasping; standing; sitting; rolling over; bowel movement; bladder evacuation; and any combination thereof.

100. The system of claim 1, wherein the system is configured to change states due to a change in state of a monitored biological signal of the patient.

101. The system of claim 100, wherein the change in system state is selected from the group consisting of: system on or off state; calibration routine on or off state; reset routine on or off state; and any combination thereof.

102. The system of claim 100, wherein the monitored biological signal is selected from the group consisting of: eye motion; eyelid motion; facial muscle activation or other electromyographic activity; heart rate; EEG; LFP; respiration; and any combination thereof.

103. The system of claim 100, wherein the monitored biological signal comprises a time code of brain activity.

104. The system of claim 1, further comprising a patient activated input device, wherein the system is configured to change state due to a signal received from the patient activated input device.

105. The system of claim 104, wherein the patient activated input device is selected from the group consisting of: chin joystick; Eyebrow EMG switch; EEG activated switch; eye tracker; head tracker; neck movement switch; shoulder movement switch; sip-n-puff joystick controller; speech recognition switch; tongue switch; and any combination thereof.

106. The system of claim 1, further comprising a light emitter, wherein the multicellular signals are received during and or after activation of the light emitter, and wherein at least one cell providing cellular signals is exposed to the emitted light.

107. The system of claim 106, wherein the light emitter comprises at least one photodiode.

108. The system of claim 106, wherein the sensor includes a photodetector that detects a photo-equivalent of a cellular signal.

109. The system of claim 106, wherein the sensor includes the light emitter.

110. The system of claim 106, wherein the light emitter emits light selected from the group consisting of: visible light; infrared light; ultraviolet light; and any combination thereof.

111. The system of claim 1, wherein the multicellular signals comprises signals emanated from the central nervous system of the patient.

112. The system of claim 1, wherein the multicellular signals comprises signals emanated from two or more cells of the patient.

113. The system of claim 1, wherein the multicellular signals comprise one or more of: neuron spikes, ECOG signals, LFP signals and EEG signals.

114. The system of claim 1, wherein at least one of the electrodes detect the multicellular signals from clusters of neurons and provide signals including a quantity of neurons between single neuron and EEG recordings.

115. The system of claim 1, wherein the processing unit is configured to utilize least one cellular signal generated under voluntary control of a patient.

116. The system of claim 1, wherein the patient comprises a human being.

117. The system of claim 1, wherein the patient is selected from the group consisting of: a quadriplegic; a paraplegic; an amputee; a spinal cord injury victim; a physically impaired person; and any combination thereof.

118. The system of claim 1, wherein the patient is healthy and/or otherwise is not utilizing the system to provide a therapeutic or restorative function.

119. The system of claim 118, wherein the controlled device comprises a piece of medical equipment.

120. The system of claim 118, wherein the controlled device comprises a communication device.

121. The system of claim 118, wherein the controlled device comprises a piece of equipment with controllable moving parts.

122. The system of claim 121, wherein the equipment is used to evacuate personnel.

123. The system of claim 121, wherein the equipment is used to diffuse a bomb.

124. The system of claim 121, wherein the equipment is used to provide a military defense function.

125. The system of claim 121, wherein the equipment is one or more of: watercraft, aircraft, land vehicle, and reconnaissance robots.

126. The system of claim 1, further comprising a second processed signal for controlling a device.

127. The system of claim 126, further comprising a second controlled device, wherein the second controlled device receives the second processed signal.

128. The system of claim 126, wherein the controlled device receives the second processed signal.

129. The system of claim 126, wherein the second processed signal is based on the multicellular signals.

130. The system of claim 129, wherein the second processed signal is based on the same set of multicellular signals as the processed signal.

131. The system of claim 126, wherein the second processed signal is based on a monitored biological signal of the patient.

132. The system of claim 131, wherein the monitored biological signal is selected from the group consisting of: eye motion; eyelid motion; facial muscle activation or other electromyographic activity; heart rate; EEG; LFP; respiration; and any combination thereof.

133. The system of claim 1, wherein the sensor includes at least one multi-electrode array comprising a plurality of electrodes.

134. The system of claim 133, wherein the array is a ten-by-ten array of electrodes.

135. The system of claim 133, wherein the multi-electrode array comprises at least one of: a recording electrode; a stimulating electrode; and an electrode having recording and stimulating capabilities.

136. The system of claim 133, wherein the sensor further comprises a second multi-electrode array.

137. The system of claim 1, wherein the sensor includes multiple wires or wire bundle electrodes.

138. The system of claim 1, wherein the sensor includes electrodes incorporated into one or more of: a subdural grid; a scalp electrode; a wire electrode; and a cuff electrode.

139. The system of claim 1, wherein the electrodes comprise wires, and the sensor comprises a wire bundle.

140. The system of claim 1, wherein the sensor includes two or more discrete components.

141. The system of claim 140, wherein each of the discrete components includes one or more electrodes.

142. The system of claim 140, wherein each of the discrete components comprises one or more of: a multi-electrode array; a wire or wire bundle; a subdural grid; and a scalp electrode.

143. The system of claim 1, wherein the sensor further comprises a signal processing circuitry.

144. The system of claim 1, wherein the sensor transmits the multicellular signals through a wireless connection.

145. The system of claim 144, wherein the sensor transmits wirelessly to a receiver mounted on the skull of the patient.

146. The system of claim 1, wherein the sensor further comprises a coil for power transmission to the sensor.

147. The system of claim 1, wherein the plurality of electrodes is capable of recording from clusters of neurons and outputting detected signals comprising multiple neuron signals.

148. The system of claim 147, wherein detected signals are a measure of the LFP response from neural activity.

149. The system of claim 147, wherein the multiple neuron signals comprise one or more of: ECoG signals, LFP signals, EEG signals and peripheral nerve signals.

150. The system of claim 149, wherein the controlled device comprises one or more of: watercraft, aircraft, land vehicle, and reconnaissance robots.

151. The system of claim 1, wherein one or more electrodes are placed into tissue selected from the group consisting of: nerve tissue; organ tissue; tumor tissue; any combination thereof.

152. The system of claim 1, wherein the processing unit includes one or more of: a temperature sensor; a pressure sensor; a strain gauge; an accelerometer; a volume sensor; an electrode; an array of electrodes; an audio transducer; a mechanical vibrator; a drug delivery device; a magnetic field generator; a photo detector element; a camera or other visualization apparatus; a wireless communication element; a light producing element; an electrical stimulator; a physiologic sensor; a heating element; and a cooling element.

153. The system of claim 1, wherein a portion of the processing unit is physically connected to the sensor.

154. The system of claim 1, wherein the processing unit comprises an integrated neuron spike sorting function.

155. The system of claim 154, wherein the neuron spike sorting function identifies spikes with a minimum amplitude threshold value.

156. The system of claim 1, wherein the processing unit comprises an element to amplify the multicellular signals.

157. The system of claim 1, wherein the signals are amplified by a gain of at least eighty.

158. The system of claim 1, wherein the processing unit utilizes one or more neural net software routines to map neural signals into the processed signals for control of the controlled device.

159. The system of claim 1, wherein the processing unit assigns one or more cellular signals to a specific use.

160. The system of claim 159, wherein the specific use is determined by the patient attempting an imagined movement or other imagined state.

161. The system of claim 1, wherein the processing unit utilizes two or more cellular signals that are mathematically combined to create the processed signal.

162. The system of claim 1, wherein the processing unit utilizes a cellular signal from a neuron whose signal is separated from other nearby neurons detected by a single electrode.

163. The system of claim 162, wherein the processing unit separates signals by neuron spike discrimination methods.

164. The system of claim 163, wherein the spike discrimination methods sort spikes by a minimum amplitude threshold value.

165. The system of claim 1, wherein the processing unit is configured to convert a monitored biological signal of the patient to a digital signal.

166. The system of claim 1, wherein a monitored biological signal of the patient is processed by the processing unit to produce a second processed signal.

167. The system of claim 166, wherein the second processed signal is used to control the controlled device.

168. The system of claim 167, wherein the second processed signal is used to modify one or more system configuration parameters of the system.

169. The system of claim 166, wherein the second processed signal is used to stop control of the controlled device.

170. The system of claim 166, wherein the second processed signal is used to reset the system.

171. The system of claim 1, wherein the controlled device is selected from the group consisting of: a computer; a computer display; a computer mouse; a computer cursor; a joystick; a personal data assistant; a robot or robotic component; a computer controlled device; a teleoperated device; a communication device; a vehicle; a wheelchair; an adjustable bed; an adjustable chair; a remote controlled device; a Functional Electrical Stimulator device; a muscle stimulator; an exoskeletal robot brace; an artificial or prosthetic limb; a vision enhancing device; a vision restoring device; a hearing enhancing device; a hearing restoring device; a movement assist device; a medical therapeutic equipment; a drug delivery apparatus; a medical diagnostic or monitoring equipment; a bladder control device; a bowel control device; a human function enhancement device; a closed loop medical equipment and other controllable devices applicable to patients with some form of paralysis or diminished function; a device that is utilized under direct brain or thought control in either a healthy or unhealthy patient; and any combination thereof.

172. The system of claim 1, further comprising a stimulating device.

173. The system of claim 172, wherein the stimulating device comprises at least an implanted portion.

174. The system of claim 172, wherein the stimulating device comprises a first discrete component and a second discrete component, the first discrete component including at least one electrode and at least one electrical connection to the second discrete component.

175. The system of claim 172, wherein the stimulating device comprises a first discrete component, and the sensor comprises a second discrete component.

176. The system of claim 172, wherein the stimulating device comprises multiple stimulating electrodes.

177. The system of claim 176, wherein the stimulating device transmits stimulating current to one or more electrodes independently.

178. The system of claim 177, wherein the stimulating device comprises a stimulating power device.

179. The system of claim 178, wherein the power device comprises an integral power supply.

180. The system of claim 178, wherein the power device comprises an integral power receiving coil.

181. The system of claim 1, wherein the system is configured to perform a permission routine for approving an operator to modify one or more integrated parameters of the system.

182. The system of claim 181, wherein the permission routine limits parameter modifications to specific operators.

183. The system of claim 182, wherein the permission routine comprises an approved operator list.

184. The system of claim 182, wherein permission to modify individual integrated parameters is linked to specific operators.

185. The system of claim 182, wherein a specific operator is permitted to approve modification of a parameter within a range of values.

186. The system of claim 185, wherein the range of values is controlled by a second operator.

187. The system of claim 181, wherein the permission routine includes multiple levels including permissions for multiple operators.

188. The system of claim 187, wherein a first operator controls a first set of one or more integrated parameters, and a second operator controls a second set of one or more integrated parameters.

189. The system of claim 188, wherein the first set of parameters includes one or more different parameters than the second set of parameters.

190. The system of claim 181, wherein the system is configured to interrogate the system to retrieve data stored therein.

191. The system of claim 181, wherein the system is configured to analyze the retrieved data to produce an output which recommends modifications to be made to at least one of the integrated parameters.

192. The system of claim 181, wherein prior to implementing a modification, the permission routine checks one or more of: username, password, and IP address.

193. The system of claim 181, wherein the permission routine includes a confirmation of modifications prior to implementing a modification.

194. The system of claim 1, wherein the system is configured to perform an adaptive processing routine.

195. The system of claim 194, wherein the adaptive processing routine includes changing over time the type or combination of types of signals processed.

196. The system of claim 195, wherein the types of signals processed include one or more of: EEG signals, ECoG signals, LFP signals, and neural spikes.

197. The system of claim 1, wherein the system is configured to perform a configuration routine for calibrating the multicellular signals.

198. The system of claim 197, wherein the configuration routine is capable of being activated by a biological signal.

199. The system of claim 197, wherein the configuration routine comprises a set of movements for configuration.

200. The system of claim 197, wherein the configuration routine comprises a video monitor.

201. The system of claim 197, wherein the configuration routine comprises a set of movements for configuration, and the video monitor is capable of displaying a selected movement.

202. The system of claim 201, wherein the movements are displayed from the patient's perspective.

203. The system of claim 197, wherein the configuration routine is capable of correlating the selected movement with a cellular signal obtained from tracking the selected movement.

204. The system of claim 197, wherein the configuration routine is capable of correlating an integrated parameter relating to the selected movement with a cellular signal obtained from tracking the selected movement.

205. The system of claim 204, wherein the parameter is one or more of: a position, a velocity, and an acceleration.

206. The system of claim 197, wherein the configuration routine includes a set of movements for configuration and the video monitor is capable of displaying a simulation of a selected movement.

207. The system of claim 206, wherein the simulation of selected movements is displayed from the patient's perspective.

208. The system of claim 1, wherein the system is configured to perform a patient feedback module to supply feedback to the patient.

209. The system of claim 208, wherein the patient feedback module comprises one or more of: an audio transducer, a tactile transducer, a visual transducer, a video display, a gustatory transducer; and an olfactory transducer.

210. The system of claim 208, wherein the patient feedback module comprises a stimulator, and one or more neurons are stimulated to cause movement or sensation in a part of the patient's body.

211. A method of producing a control signal for use in a biological interface system, comprising:
- detecting multicellular signals emanating from one or more living cells of a patient;
- processing the detected multicellular signals to produce a processed signal;
- generating an alternative signal;
- providing a signal gate configured to receive the processed signal and the alternative signal, the signal gate selectively transmitting either the processed signal or the alternative signal to a controlled device as a control signal;
- monitoring a status of a biological interface system and producing a system status signal; and
- determining, based on the system status signal, which of the processed signal and the alternative signal is to be transmitted to the controlled device.

* * * * *